US012297223B2

(12) United States Patent
Bishop et al.

(10) Patent No.: US 12,297,223 B2
(45) Date of Patent: May 13, 2025

(54) COMPOUNDS

(71) Applicants: GLAXOSMITHKLINE INTELLECTUAL PROPERTY DEVELOPMENT LIMITED, Middlesex (GB); FIMBRION THERAPEUTICS, INC., Saint Louis, MO (US)

(72) Inventors: Michael Joseph Bishop, Collegeville, PA (US); James Walter Janetka, Saint Louis, MO (US); Laurel Kathryn McGrane, Saint Louis, MO (US); Eugene Lee Stewart, Collegeville, PA (US); Katherine Louisa Widdowson, Collegeville, PA (US)

(73) Assignees: GlaxoSmithKline Intellectual Property Development Limited, Stevenage (GB); Fimbrion Therapeutics, Inc., Saint Louis, MI (US)

( * ) Notice: Subject to any disclaimer, the term of this patent is extended or adjusted under 35 U.S.C. 154(b) by 502 days.

(21) Appl. No.: 17/606,134

(22) PCT Filed: May 6, 2020

(86) PCT No.: PCT/EP2020/062501
§ 371 (c)(1),
(2) Date: Oct. 25, 2021

(87) PCT Pub. No.: WO2020/225273
PCT Pub. Date: Nov. 12, 2020

(65) Prior Publication Data

US 2022/0298197 A1 Sep. 22, 2022

Related U.S. Application Data

(60) Provisional application No. 62/844,215, filed on May 7, 2019.

(51) Int. Cl.
*C07H 15/26* (2006.01)
*C07H 15/207* (2006.01)

(52) U.S. Cl.
CPC .......... *C07H 15/26* (2013.01); *C07H 15/207* (2013.01)

(58) Field of Classification Search
None
See application file for complete search history.

(56) References Cited

U.S. PATENT DOCUMENTS

| | | | |
|---|---|---|---|
| 6,153,396 | A | 11/2000 | Hultgren |
| 6,962,791 | B2 | 11/2005 | Hultgren |
| 7,790,183 | B2 | 9/2010 | Darouiche |
| 8,937,167 | B2 | 1/2015 | Janetka |
| 9,567,362 | B2 | 2/2017 | Janetka |
| 9,957,289 | B2 | 5/2018 | Janetka |
| 10,273,260 | B2 | 4/2019 | Janetka |
| 10,738,070 | B2 | 8/2020 | Janetka et al. |
| 11,111,262 | B2 | 9/2021 | Bishop et al. |
| 11,697,665 | B2 | 7/2023 | Bishop et al. |
| 2007/0167378 | A1 | 7/2007 | Saraiva |
| 2008/0171706 | A1 | 7/2008 | Berglund |
| 2008/0268006 | A1 | 10/2008 | Molin |
| 2010/0015600 | A1 | 1/2010 | Barnich |
| 2012/0309701 | A1 | 12/2012 | Janetka |
| 2014/0243283 | A1 | 8/2014 | Ramtohul et al. |
| 2014/0274930 | A1 | 9/2014 | Dietrich |
| 2015/0175644 | A1 | 6/2015 | Ernst |
| 2015/0197538 | A1 | 7/2015 | Janetka |
| 2016/0145289 | A1 | 5/2016 | Janetka |
| 2017/0247401 | A1 | 8/2017 | Janetka |
| 2018/0194792 | A1 | 7/2018 | Janetka |
| 2019/0106451 | A1 | 4/2019 | Janetka |
| 2019/0211045 | A1 | 7/2019 | Janetka |
| 2020/0002303 | A1 | 1/2020 | Janetka |
| 2021/0208430 | A1 | 7/2021 | Liu et al. |

FOREIGN PATENT DOCUMENTS

| | | | |
|---|---|---|---|
| EP | 383092 | | 1/1990 |
| EP | 0383092 | A2 | 3/1992 |
| WO | WO/1995/014028 | | 5/1995 |
| WO | WO/2001/10386 | | 2/2001 |
| WO | WO/2005/089733 | | 9/2005 |
| WO | WO 2011/050323 | A1 | 4/2011 |
| WO | WO/2011/073112 | | 6/2011 |
| WO | WO/2012/109263 | | 8/2012 |
| WO | WO/2012/164074 | | 12/2012 |
| WO | WO 2013/134415 | | 9/2013 |
| WO | WO 2014/016361 | | 1/2014 |
| WO | WO 2014/055474 | | 4/2014 |
| WO | WO 2014/100158 | | 6/2014 |
| WO | WO 2014/165107 | | 10/2014 |
| WO | WO/2014/194270 | | 12/2014 |
| WO | WO 2014/194270 | A1 | 12/2014 |
| WO | WO/2017/021549 | | 2/2017 |
| WO | WO/2017/156508 | | 9/2017 |
| WO | WO/2017/165619 | | 9/2017 |
| WO | WO/2019/076931 | | 4/2019 |

OTHER PUBLICATIONS

Abdel-Megeid, F. et al., "Preparation and Some Reactions of O-Glucosyl Derivatives of 2-Thioxo-1,3,4-Oxadiazoles and 2-Thioxo-1,3,4-Thiadiazoles and Their 2-Oxo Analogues", Carbohydrate Res., 59(1):95-102, (1977).

Abgottspon, D. et al., "Development of an Aggregation Assay to Screen FimH Antagonists", J Microb Methods, 82(3):249-55, (2010).

Abgottspon, D. et al., "In Vivo Evaluation of FimH Antagonists—A Novel Class of Antimicrobials for the Treatment of Urinary Tract Infection", Chimia, 66(4):166-9, (2012).

(Continued)

*Primary Examiner* — Layla D Berry
(74) *Attorney, Agent, or Firm* — Nora L. Stein

(57) ABSTRACT

Disclosed herein are new C-mannoside compounds and compositions and their application as pharmaceuticals for the treatment of human disease. Methods of inhibition of FimH activity in human subjects are also provided for the treatment diseases such as urinary tract infection.

20 Claims, No Drawings

(56) References Cited

OTHER PUBLICATIONS

Almant M, Moreau V, Kovensky J, et al. "Clustering of *Escherichia coli* type-1 fimbrial adhesins by using multimeric heptyl a-D-mannoside probes with a carbohydrate core," Chem Eur J,17:10029-10038 (2011).
Aronson M, Medalia O, Schori L, et al. "Prevention of colonization of the urinary tract of mice with *Escherichia coli* by blocking of bacterial adherence with methyl alpha-D-mannopyranoside," J Infect Dis, 139:329-332 (1979).
Barras A, Martin FA, Bande O, et al. "Glycan-functionalized diamond nanoparticles as potent *E. coli* anti-adhesives," Nanoscale,5:2307-2316 (2013).
Bognar, R. et al., "N-Glycosyl Derivatives: Part I11. The Subsequent Installation of the Aglycone. Synthesis of N- Glycosyl Derivatives of 2-Amino-Thiazole, 2-Amino-1 ,3,4-Thiadiazole and 5-Amino-1 ,2,3,4-Thiatriazols", Carbohy Res., 5:320-328, (1967).
Bouckaert, J. et al., "Receptor Binding Studies Disclose a Novel Class of High-Affinity Inhibitors of the *Escherichia coli* FimH Adhesion", Mol Microbial., 55(2):441-55, (2005).
Bouckaert J, Li Z, Xavier C, et al. "Heptyl alpha-D-mannosides grafted on a beta-cyclodextrin core to interfere with *Escherichia coli* adhesion: an in vivo multivalent effect," Chemistry,19:7847-7855 (2013).
Car Z, Hrenar T, Petrović Peroković VP, et al. "Mannosylated N-aryl substituted 3- hydroxypyridine-4-ones: synthesis, hemagglutination inhibitory properties, and molecular modeling," Chem Biol Drug Des, 84:393-401 (2014).
Chandrasekaran V, Kolbe K, Beiroth F, et al. "Synthesis and testing of the first azobenzene mannobioside as photoswitchable ligand for the bacterial lectin FimH," Beilstein J Org Chem, 9:223-233 (2013).
Choudhury D, Thompson A, Stojanoff V, et al. "X-ray structure of the FimC-FimH chaperone-adhesin complex from uropathogenic *Escherichia coli*," Science,285:1061-1066 (1999).
Cusumano, C. et al., "Treatment and Prevention of Urinary Tract Infection with Orally Active FimH Inhibitors", Sci Transl Med., 3(109):109ra115, (2011).
De Ruyck J, Lensink MF, Bouckaert J, "Structures of C-mannosylated anti-adhesives bound to the type 1 fimbrial FimH adhesin," IUCrJ,3(Pt 3:163-167 (2016).
Durka, M. et al., "The Functional Valency of Dodecamannosylated Fullerenes with *Escherichia coli* FimH-Towards Novel Oacterial Antiadhesives", Chem Commun., 47(4):1321-3, (2011).
Firon, N. et al., "Aromatic Alpha-Glycosides of Mannose Are Powerful Inhibitors of the Adherence of Type 1 Fimbriated *Escherichia coli* to Yeast and Intestinal Epithelial Cells", Infect Immun., 55(2):472-6, (1987).
Firon, N. et al., "Interaction of Mannose-Containing Oligosaccharides With the Fimbrial Lectin of *Escherichia coli*", Biochem and Biophys Res Commun., 105(4):1426-32, (1982).
Furneaux, R. et al., "New Mannotriosides and Trimannosides as Potential Ligands for Mannose—Specific Binding Oroteins", Can J Chem., 80:964-72, (2002).
Gouin, S. et al., "Synthetic Multimeric Heptyl Mannosides as Potent Antiadhesives of Uropathogenic *Escherichia coli*", Chem Med Chem., 4(5):749-55, (2009).
Grabosch, C. et al., "Squaric Acid Monoamide Mannosides as Ligands for the Bacterial Lectin FimH: Covalent nhibition or Not?", Chem Bio Chem., 12(7):1066-74, (2011).
Guiton, P. et al., "Combinatorial Small-Molecule Therapy Prevents Uropathogenic *Escherichia coli* Catheter-Associated Urinary Tract Infections in Mice", Antimicrob Agents Chemother., 56(9):4738-45, (2012).
Han, Z. et al., "Lead Optimization Studies on FimH Antagonists: Discovery of Potent and Orally Bioavailable Ortho-Substituted Biphenyl Mannosides", J Med Chem., 55(8):3945-59, (2012).
Han, Z. et al., "Structure-Based Drug Design and Optimization of Mannoside Bacterial FimH Antagonists", J Med Chem., 53(12):4779-92, (2010).
Hartmann, M. et al., "The Bacterial Lectin FimH, a Target for Drug Discovery—Carbohydrate Inhibitors of Type 1 Fimbriae-Mediated Bacterial Adhesion", Eur J Org Chem., 2011(20-21):3583-3609 (2011).
Haskins, W. et al., "Relations Between Rotatory Power and Structure in the Sugar Group; Some 2'-Naphthyl L-Thioglycopyranosides and their Acetates", J Am Chem Soc., 69(7):1668-72, (1947).
Hung, C. et al., "Structural Basis of Tropism of *Escherichia coli* to the Bladder During Urinary Tract Infection", Mol Microb., 44(4):903-15, (2002).
Irani, R. et al., "Stannic Chloride Promoted Synthesis of Mannosides", Indian J Chem., Sect. B: Org. Chem. Incl. Med. Chem. 30(5):519-21, (1991), (abstract only).
Jarvis C, Han Z, Kalas V, et al., "Antivirulence isoquinolone mannosides: optimization of the biaryl aglycone for FimH lectin binding affinity and efficacy in the treatment of chronic UTI," ChemMedChem,11(4):367-373 (2016).
Jiang, X. et al., "Antiadhesion Therapy for Urinary Tract Infections—A Balanced PK/PD Profile Proved to Be Key for Success", J Med Chem., 55(10):4700-13, (2012).
Kleeb S, Jiang X, Frei P, et al., "FimH antagonists: phosphate prodrugs improve oral bioavailability," J Med Chem, 59(7):3163-3182 (2016).
Kleeb S, Pang L, Mayer K, et al., "FimH antagonists: bioisosteres to improve the in vitro and in vivo PK/PD profile," J Med Chem, 58(5):2221-2239 (2015).
Klein, T. et al., "FimH Antagonists for the Oral Treatment of Urinary Tract Infections: From Design and Synthesis to in Vitro and in Vivo Evaluation", J Med Chem., 53(24):8627-41, (2010).
Kostakioti, M. et al., "Distinguishing the Contribution of Type 1 Pili from That of other QseB—Misregulated Factors When QseC is Absent during Urinary Tract Infection", Infect Immun., 80(8):2826-34, (2012).
Kötter S, Krallmann-Wenzel U, Ehlers S, et al., "Multivalent ligands for the mannose-specific lectin on type 1 fimbriae of *Escherichia coli*: syntheses and testing of trivalent a-D-mannoside clusters," J Chem Soc Perkin Trans I,14:2193-2200 (1998).
Lindhorst, T. et al., "Inhibition of the Type 1 Fimbriae-Mediated Adhesion of *Escherichia coli* to Erythrocytes by Multiantennary [alpha]-mannosyl Clusters: The Effect of Multivalency", Glycoconj J., 15(6):605-13, (1998).
Lindhorst TK, Bruegge K, Fuchs A, et al., "A bivalent glycopeptide to target two putative carbohydrate binding sites on FimH," Beilstein J Org Chem,6:801-809 (2010).
Nagahori, N. et al., "Inhibition of Adhesion of Type 1 Fimbriated *Escherichia coli* to Highly Mannosylated Ligands", ChemBioChem, 3(9):836-44, (2002).
Neeser J, Koellreutter B, Wuersch P, "Oligomannoside-type glycopeptides inhibiting adhesion of *Escherichia coli* strains mediated by type 1 pili: preparation of potent inhibitors from plant glycoproteins," Infect Immun,52(4):428-436 (1986).
Pang, et al., "FimH Antagonists: Structure-Activity and Structure-Property Relationships for Biphenyla-D-Mannopyranosides," ChemMedChem 2012, vol. 7, pp. 1404-1422, p. 1408.
Papadopoulos A, Shiao TC, Roy R, "Diazo transfer and click chemistry in the solid phase syntheses of lysine-based glycodendrimers as antagonists against *Escherichia coli* FimH," Mol Pharm,9:394-403 (2012).
Qian, X. et al., "Arrays of Self-Assembled Monolayers for Studying Inhibition of Bacterial Adhesion", Anal Chem., 74(8):1805-10, (2002).
Rabbani, S. et al., "Expression of the Carbohydrate Recognition Domain of FimH and Development of a Competitive Binding Assay", Anal Biochem., 407(2):188-95, (2010).
Sattigeri, J. et al., "Synthesis and Evaluation of Thiomannosides, Potent and Orally Active FimH Inhibitors", Bioorg Med Chem Lett., 28(17):2993-2997, (2018).
Scharenberg, M. et al., "Target Selectivity ofFimH Antagonists", J Med Chem., 55(22):9810-6, (2012).
Scharenberg, M. et al., "A Flow Cytometry-Based Assay for Screening FimH Antagonists", Assay Drug DevTechnol., 9(5):455-65, (2011).

(56) References Cited

OTHER PUBLICATIONS

Schierholt A, Hartmann M, Lindhorst TK, “Bi- and trivalent glycopeptide mannopyranosides as inhibitors of type 1 fimbriae-mediated bacterial adhesion: variation of valency, aglycon and scaffolding,” Carb Res,346:1519-1526 (2011).
Schönemann W, Kleeb S, Dätwyler P, et al., Prodruggability of carbohydrates—oral FimH antagonists, Can J Chem,94 (11):909-919 (2016).
Schonemann, et al., “Improvement of Agylcone π-Stacking Yields Nanomolar to Sub-nanomolar FimH Antagonists,” *ChemMedChem*, 14(7):749-757 (2019).
Schwardt, 0. et al., “Design, Synthesis and Biological Evaluation of Mannosyl Triazoles as FimH Antagonists”, Bioorg Med Chem., 19(21):6454-73, (2011).
Shuman, D. et al., “Synthesis and Biological Activity of Certain 8-Mercaptopurine and 6- Mercaptopyrimidine S-Nucleosides”, J Med Chem., 12(4):653-7, (1969).
Sperling, O. et al., “Evaluation of the Carbohydrate Recognition Domain of the Bacterial Adhesion FimH: Design, Synthesis and Binding Properties of Mannoside Ligands”, Org Biomol Chem., 4(21):3913-3922, (2006).
Stoll, Van A. et al., “The Furocoumarin and the Beta-D-Glucosido-Furocumarinsaure from the Seeds of *Coronilla* Species”, Helvetica Chimica Acta, 33(211-212):1637-47, (1950), (with English abstract).
Taile, V. et al., “Synthesis and Biological Evaluation of Novel 2(4-O-beta-D glucosidoxyphenyl) 4,5-Disubstituted Imidazoles”, J Heterocyclic Chem., 47(4):903-7, (2010).
Tomaić T, Rabbani S, Gobec M, et al., “Branched: a-D-mannopyranosides: a new class of potent FimH antagonists,” Med Chem Commun,5(8):1247-1253 (2014).
Touaibia, M. et al., “Glycodendrimers as Anti-Adhesion Drugs Against Type 1 Fimbriated *E. coli* Uropathogenic Infections”, Mini Rev Med Chem., 7(12):1270-83, (2007).
Touaibia, M. et al., “Mannosylated G(0) Dendrimers with Nanomolar Affinities to *Escherichia coli* FimH”, ChemMedChem., 2(8):1190-1201, (2007).
Touaibia, M. et al., “Tri- and Hexavalent Mannoside Clusters as Potential Inhibitors of Type 1 Fimbriated Bacteria Using Pentaerythritol and Triazole Linkages”, Chem Commun., (4):380-2, (2007).
Walter, M. et al., “A Modular System for the Preparation of Diazirine-Labeled Mannose Derivatives Using Thiourea Bridging”, Synthesis, 6:952-8, (2006).
Wellens, A. et al., “Intervening with Urinary Tract Infections Using Anti-Adhesives Based on the Crystal Structure of the FimH-Oligomannose-3 Complex”, PLoS ONE, 3(4):e2040, (2008).
Written Opinion and International Search Report issued in PCT/IB2019/055806, dated Oct. 16, 2019.
International Preliminary Report on Patentability issued in PCT/IB2019/055806, dated Jun. 5, 2020.
Laurel Mydock-McGrane, et al. “Antivirulence C-Mannosides as Antibiotic-Sparing, Oral Therapeutics for Urinary Tract Infections”. Journal of Medicinal Chemistry, vol. 59, No. 20, 9390-9408 (Oct. 14, 2016).
Banker, G., et al., “Modern Pharmaceuticals, 3ed.”, Marcel Dekker, New York, p. 596, 1996.
Fatima, et al., “Application of butenonyl-C-glucosides in the synthesis of pyrazolinyl-, aminopyrimidinyl- and biphenyl methyl-ß-d-C-glucopyranosides”, Molecular Diversity, 15(3), 759-768, 2011.
Gouin, S. et al., “Discovery and Application of FimH Antagonists”, Top Med Chem., vol. 12, pp. 123-168, DOI: 10.1007/7355_2014_52 (2014).
Torres, et al., “Crohn’s Disease”, The Lancet, vol. 389, pp. 1741-1755, DOI: 10.1016/S0140-6736(16)31711-1 (2016).
Wolff, M., “Burger’s Medical Chemistry, 5 ed., Part 1”, John Wiley & Sons, pp. 975-977, (1995).
Notice of Allowance and Fee(s) Due related to U.S. Appl. No. 13/453,991, dated Sep. 4, 2014, 11 pages.
Notice of Allowance and Fee(s) Due related to U.S. Appl. No. 13/453,991, dated Jul. 14, 2014, 8 pages.
Notice of Allowance and Fee(s) Due related to U.S. Appl. No. 14/570,322, dated Sep. 9, 2016, 8 pages.
Office Action from U.S. Appl. No. 13/453,991, dated Mar. 6, 2014, 9 pages.
Office Action from U.S. Appl. No. 13/453,991, dated Nov. 20, 2013, 14 pages.
Office Action from U.S. Appl. No. 14/570,322, dated May 20, 2016, 8 pages.
U.S. Appl. No. 13/453,991; Notice of Allowance, dated Jul. 14, 2014; 4 pages.
U.S. Appl. No. 13/453,991; Notice of Allowance, dated Sep. 4, 2014; 4 pages.
U.S. Appl. No. 13/453,991; Office Action, dated Mar. 6, 2014; 9 pages.
U.S. Appl. No. 13/453,991; Office Action, dated Nov. 20, 2013; 12 pages.
U.S. Appl. No. 14/570,322; Notice of Allowance, dated Sep. 9, 2016; 7 pages.
U.S. Appl. No. 14/570,322; Office Action, dated May 20, 2016; 8 pages.
U.S. Appl. No. 14/894,927; Notice of Allowance, dated Aug. 16, 2017; 5 pages.
U.S. Appl. No. 14/894,927; Notice of Allowance, dated Dec. 8, 2017; 7 pages.
U.S. Appl. No. 14/894,927; Office Action, dated Mar. 3, 2017; 10 pages.
U.S. Appl. No. 15/373,260; Notice of Allowance, dated Jul. 2, 2018; 4 pages.
U.S. Appl. No. 15/373,260; Notice of Allowance, dated Nov. 21, 2018; 7 pages.
U.S. Appl. No. 15/373,260; Notice of Allowance, dated Oct. 23, 2018; 7 pages.
U.S. Appl. No. 15/373,260; Office Action, dated Feb. 26, 2018; 5 pages.
U.S. Appl. No. 15/915,490; Office Action, dated Aug. 29, 2019; 12 pages.
U.S. Appl. No. 16/087,305; Non-Final Office Action, dated Dec. 31, 2019; 19 pages.
U.S. Appl. No. 16/353,824; Office Action, dated Nov. 6, 2019; 7 pages.
U.S. Appl. No. 16/087,305; Application as filed, dated Sep. 21, 2018, 80 pages.

COMPOUNDS

This application is a § 371 of International Application No. PCT/EP2020/062501, filed 6 May 2020, which claims the benefit of U.S. Provisional Application No. 62/844,215, filed 7 May 2019.

STATEMENT REGARDING FEDERALLY SPONSORED RESEARCH OR DEVELOPMENT

This invention was made with government support under Award Number R44AI106112 awarded by the National Institute of Allergy and Infectious Diseases of the National Institutes of Health. The government has certain rights in the invention.

FIELD OF THE INVENTION

Disclosed herein are new C-mannoside compounds and compositions and their application as pharmaceuticals for the treatment of human disease. Methods of inhibition of FimH activity in a human subject are also provided for the treatment diseases such as urinary tract infection.

BACKGROUND OF THE INVENTION

Urinary tract infection (UTI) is one of the most common infectious diseases in women. The morbidity and economic impact are enormous, with over $2.5 billion spent annually on treatment. Further, recurrent infections are a significant problem despite appropriate antibiotic therapy of the initial infection case. Women who present with an initial episode of acute UTI have a 25-44% chance of developing a second and a 3% chance of experiencing three episodes within six months of the initial UTI. Furthermore, resistance to antibiotics commonly prescribed to treat or prevent UTI is spreading rapidly among uropathogens, highlighting the need for new antibiotic-sparing and -enabling therapies.

Greater than 85% of UTI are caused by uropathogenic *Escherichia coli* (UPEC). Gram-negative bacteria such as UPEC are the causative agents of a wide variety of acute and chronic infectious diseases. Many of these infections are initiated by a critical interaction between host ligands (frequently polysaccharide moieties) and bacterial adhesins (frequently expressed at the distal tip of polymeric pilus fibers assembled by the chaperone-usher pathway). Animal models of UTI have revealed that the mannose-binding FimH adhesin of type 1 pili is critical for the colonization of and invasion into the bladder epithelium by UPEC, as well as other uropathogenic members of the Enterobacteriaceae family, such as *Klebsiella, Enterobacter*, and *Citrobacter* species.

Type 1 pili are anchored in the bacterial outer membrane and are largely composed of repeating FimA protein subunits which form a helically wound cylinder that comprises the thick pilus rod. The distal FimH adhesin protein is connected to the pilus rod by the flexible tip fibrillum, which is composed of one copy each of FimF and FimG. The adhesin tip protein FimH is a two-domain protein comprised of a pilin domain ($FimH_P$), which allows it to incorporate into the pilus, and a lectin domain ($FimH_L$) that contains a conserved mannose binding pocket. The X-ray crystal structure of FimH bound to mannose showed that mannose is bound in a negatively charged pocket on FimH. The mannose binding site is highly conserved as it is invariant in 300 fimH genes sequenced from clinical UPEC strains. It is the interaction of FimH with mannosylated host proteins that is believed to mediate colonization of the lower urinary tract by UPEC and other Enterobacteriaceae during UTI.

To elucidate the molecular details of UPEC pathogenesis, several murine models of infection have been established which recapitulate many of the clinical manifestations often seen in humans. These models include acute UPEC infections, chronic and/or recurrent infections, and catheter-associated UTI. In all of these models the adhesin FimH has been shown to play an integral role in pathogenesis, highlighting it as an excellent therapeutic target. The fundamental interaction between FimH and the host is believed to occur with binding to high-mannose containing glycans, such as uroplakins and other proteins expressed on the surface of bladder epithelial cells, that coat the luminal surface of the bladder. This initial binding facilitates bacterial colonization of the bladder epithelium and invasion of the bacteria into the bladder epithelial cells. Once internalized, a single bacterium that escapes into the host cell cytoplasm can rapidly replicate and progress to form a biofilm-like intracellular bacterial community (IBC). Once these communities reach maturation they are able to disperse and escape from the cell, filamenting to evade neutrophil phagocytosis. These filamentous bacteria can then go on to infect neighboring cells, reinitiating IBC formation and the pathogenic cycle. Importantly, evidence of IBCs and bacterial filaments has been observed in the urine of women suffering with an acute UTI, supporting the validity of the mouse model in recapitulating human disease.

In contrast to UTI, which is primarily mediated by a bacterial pathogen, the disease manifested in patients suffering from idiopathic inflammatory bowel disease (IBD), such as Crohn's disease (CD) and ulcerative colitis (UC), is the result of a complex interplay between a genetically susceptible host, a dysfunctional immune system, and a microbial component. Examination of biopsied tissue from patients suffering from CD and UC has highlighted an increase in the abundance of *E. coli* associated with gut mucosa. Analysis of these bacteria has resulted in discovery of a distinct pathotype known as adherent and invasive *E. coli* (AIEC), though a portion of these strains appear similar genomically to UPEC. Identification of AIEC and their putative role in CD and UC has led to a number of follow up studies by several independent groups examining the intestinal microbiota in patients with IBD. This work has provided substantial evidence for the overgrowth of AIEC in ileal CD patients, with less convincing data for other IBD subtypes, including UC, colonic CD, and ileocolonic CD. Analysis of ileal enterocytes isolated from CD patients identified abnormal expression of the host receptor carcinoembryonic antigen-related cell adhesion molecule 6 (CEACAM6), which is highly mannosylated and been demonstrated to facilitate binding of AIEC to these cells via type 1 pili. Interestingly, adherence and invasion of AIEC into intestinal epithelial cells leads to increased expression of the receptor CEACAM6, suggesting AIEC are able to promote their own colonization of the ileum in CD patients. Utilization of a transgenic mouse expressing human CEA family gene cluster, including CEACAM6, results in increased colonization of AIEC, which recapitulates many of the clinical symptoms of CD including severe colitis, weight loss, and in this model decreased survival. Furthermore, these symptoms can be completely abolished through the administration of an anti-CEACAM6 antibody or through the genetic deletion of FimH in the bacterial strain, demonstrating a direct link between the recognition of CECAM6 by FimH and disease progression. Therefore, therapies targeting FimH among AIEC could have great benefit in relieving symptoms in CD patients.

SUMMARY OF THE INVENTION

Novel compounds and pharmaceutical compositions, which have been found to inhibit FimH have been discovered, together with methods of synthesizing and using the compounds including methods for the treatment of FimH-mediated diseases in a patient by administering the compounds.

More specifically, in one embodiment, the present invention relates to a compound of formula I, or a pharmaceutically acceptable salt thereof

I

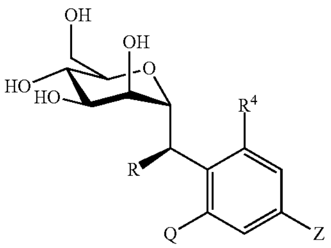

in which

Z is

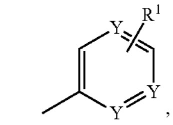,
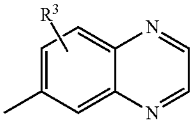,
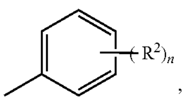, or
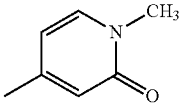;

n=1 to 3;

Q is $CF_3$, $CH_3$ or Cl;

R is $C_{1-3}$alkyl (optionally substituted with up to 7 fluorine atoms), $C_{2-6}$alkynyl, phenyl, $-(CH_2)_m-OH$, optionally substituted cyclopropyl, or optionally substituted vinyl;

$R^1$, $R^2$, and $R^3$ are independently H, F, Cl, Br, $C_{3-6}$cycloalkyl, OR', $-N(C_{1-6}alkyl)_2$, $C_{2-6}$alkenyl, $C_{2-6}$alkynyl, $C_{1-6}$alkyl (optionally substituted with up to 7 fluorine atoms, up to one hydroxy, up to one $-N(C_{1-6}\ alkyl)_2$, and up to one $-OC_{1-6}$alkyl), up to one $-(CO)-NH-CH_3$, or up to one cyano;

provided $R^2$ cannot be all H at the same time;

$R^4$ is H or F;

R' is independently H or $C_{1-6}$ alkyl (optionally substituted with up to 7 fluorine atoms);

Y is independently CH, N or, where permitted by the structure of Z, $CR_1$, provided all Y's cannot be CH at the same time; and m=1 to 3.

In one embodiment, the present invention relates to a compound of formula I, or a pharmaceutically acceptable salt thereof:

I

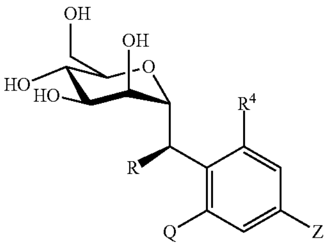

in which

Z is

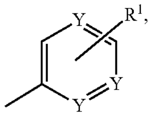,
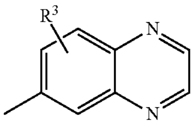,
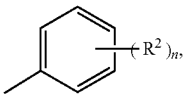, or
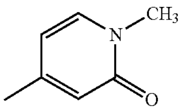;

n=1 to 3;

Q is $CF_3$, $CH_3$ or Cl;

R is $C_{1-3}$alkyl (optionally substituted with up to 7 fluorine atoms), $C_{2-6}$alkynyl, phenyl, $-(CH_2)_m-OH$, optionally substituted cyclopropyl, or optionally substituted vinyl;

$R^1$, $R^2$, and $R^3$ are independently H, F, Cl, Br, $C_{3-6}$cycloalkyl, OR', $-N(C_{1-6}alkyl)_2$, $C_{2-6}$alkenyl, $C_{2-6}$alkynyl, $C_{1-6}$alkyl (optionally substituted with up to 7 fluorine atoms, up to one hydroxy, up to one $-N(C_{1-6}\ alkyl)_2$, and up to one $-OC_{1-6}$alkyl), up to one $-(CO)-NH-CH_3$, or up to one cyano; provided $R^2$ cannot be all H at the same time;

$R^4$ is H or F;

R' is independently H or $C_{1-6}$ alkyl (optionally substituted with up to 7 fluorine atoms);

Y is independently C, CH or N, provided all Y's cannot be CH at the same time; and m=1 to 3.

For the avoidance of doubt, the general formula (I) below:

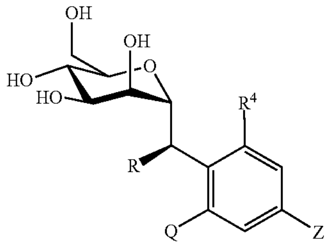

may also be represented as follows:

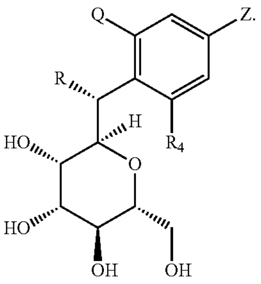

Also, for the avoidance of doubt, the substituents $R^1$, $R^2$, and $R^3$ may be independently selected from the list consisting of: H, F, Cl, Br, $C_{3-6}$cycloalkyl, OR', —N($C_{1-6}$alkyl)$_2$, $C_{2-6}$alkenyl, $C_{2-6}$alkynyl, —(CO)—NH—$CH_3$, cyano and $C_{1-6}$alkyl, wherein said $C_{1-6}$alkyl is optionally substituted with up to 7 fluorine atoms, up to one hydroxy, up to one —N($C_{1-6}$ alkyl)$_2$, and up to one —O$C_{1-6}$alkyl with the proviso that at least one $R_2$ group is not H, and with the proviso that only one $R_2$ group may be —(CO)—NH—$CH_3$ or cyano.

In one embodiment, R is $C_{1-3}$alkyl (optionally substituted with up to 7 fluorine atoms), $C_{2-6}$alkynyl, phenyl, —$(CH_2)_m$—OH, optionally substituted cyclopropyl, or optionally substituted vinyl.

In one embodiment, R is $C_{1-3}$alkyl (optionally substituted with up to 7 fluorine atoms), $C_{2-6}$alkynyl, phenyl, —$(CH_2)_m$—OH, cyclopropyl, or vinyl.

In one embodiment, R is $C_{1-3}$alkyl, phenyl, —$(CH_2)_m$—OH, cyclopropyl, ethynyl, or vinyl.

In one embodiment, R is methyl, ethyl, isopropyl, phenyl, —$(CH_2)_m$—OH, cyclopropyl, ethynyl, or vinyl.

In one embodiment, R is methyl or vinyl.

In one embodiment, R is methyl.

In one embodiment, Q is $CF_3$ or $CH_3$. In one embodiment, Q is $CH_3$. In one embodiment $R^4$ is H.

In one embodiment, either Q is $CH_3$ and R4 is H, or Q is $CF_3$ and $R^4$ is H. In one embodiment, Q is $CH_3$ and $R^4$ is H.

In one embodiment, $R^1$ is F, cyclopropyl, —$CF_3$, or cyano. In one embodiment, $R^1$ is cyclopropyl, —$CF_3$, or cyano. In one embodiment, $R^1$ is —$CF_3$.

In one embodiment, $R^2$ is independently —$CF_3$, —F, —Cl, —Br, cyano, —(CO)—NH—$CH_3$, —$CH_2$—$CH_2$—OH, hydrogen, or cyclopropyl; provided $R^2$ cannot be all hydrogen at the same time.

In one embodiment, $R^2$ is independently —F, —Cl, cyano or —(CO)—NH—$CH_3$. In one embodiment, $R^2$ is F or Cl.

In one embodiment, $R^3$ is F, Cl, or Br. In one embodiment, $R^3$ is F.

In one embodiment, Z is:

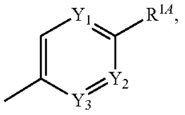

,

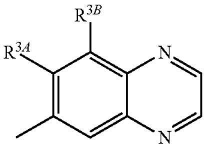

,

-continued

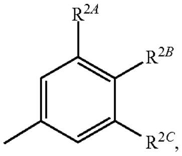

or

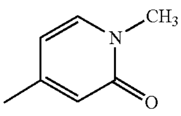

;

wherein $Y_1$ is N or $CR^{1B}$ and $Y_2$ and $Y_3$ are selected from the group consisting of N or CH, with the proviso that at least one of $Y_1$, $Y_2$ and $Y_3$ is N; and wherein $R^{1A}$, $R^{1B}$, $R^{2A}$, $R^{2B}$, $R^{2C}$, $R^{3A}$ and $R^{3B}$ are independently selected from the group consisting of H, F, Cl, Br, $C_{3-6}$cycloalkyl, OR', —N($C_{1-6}$alkyl)$_2$, $C_{2-6}$alkenyl, $C_{2-6}$alkynyl, —(CO)—NH—$CH_3$, cyano and $C_{1-6}$alkyl, wherein said $C_{1-6}$alkyl is optionally substituted with up to 7 fluorine atoms, up to one hydroxy, up to one —N($C_{1-6}$ alkyl)$_2$, and up to one —O$C_{1-6}$alkyl with the provisos that:

where $Y_1$ is $CR^{1B}$, one of $R^{1A}$ and $R^{1B}$ is H;

one of $R^{3A}$ and $R^{3B}$ is H;

at least one of $R^{2A}$, $R^{2B}$ and $R^{2C}$ is not H; and only one of $R^{2A}$, $R^{2B}$ and $R^{2C}$ may be —(CO)—NH—$CH_3$ or cyano.

In one embodiment, $R^{1A}$, $R^{1B}$, $R^{2A}$, $R^{2B}$, $R^{2C}$, $R^{3A}$ and $R^{3B}$ are independently selected from the group consisting of H, F, Cl, $CF_3$, cyclopropyl, —(CO)—NH—$CH_3$ and cyano, with the provisos that:

where $Y_1$ is $CR^{1B}$, one of $R^{1A}$ and $R^{1B}$ is H;

one of $R^{3A}$ and $R^{3B}$ is H;

at least one of $R^{2A}$, $R^{2B}$ and $R^{2C}$ is not H; and only one of $R^{2A}$, $R^{2B}$ and $R^{2C}$ may be —(CO)—NH—$CH_3$ or cyano.

In one embodiment, Z is:

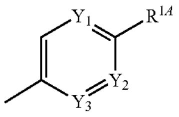

or

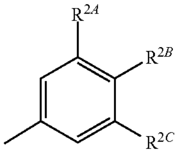

wherein $Y_1$, $Y_2$, $Y_3$, $R^{1A}$, $R^{2A}$, $R^{2B}$ and $R^{2C}$ are as defined herein.

In one embodiment, Z is:

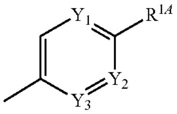

wherein $Y_1$, $Y_2$, $Y_3$ and $R^{1A}$, are as defined herein.

In one embodiment, $Y_1$ and $Y_3$ are N and $Y_2$ is CH. In a particular embodiment where $Y_1$ and $Y_3$ are N and $Y_2$ is CH, $R^{1A}$ is selected from the group consisting of F, cyclopropyl, —$CF_3$, or cyano. In one embodiment, $R^{1A}$ is cyclopropyl or —$CF_3$. In one embodiment, $R^{1A}$ is —$CF_3$.

In an alternative embodiment, $Y_3$ is N, $Y_2$ is CH and $Y_1$ is $CR^{1B}$. In a particular embodiment where $Y_3$ is N, $Y_2$ is CH, Y1 is $CR^{1B}$, one of $R^{1A}$ and $R^{1B}$ is H and the other is selected from the group consisting of F, cyclopropyl, —$CF_3$, or cyano. In one embodiment, one of $R^{1A}$ and $R^{1B}$ is H and the other is selected from the group consisting of cyclopropyl, —$CF_3$, or cyano.

In one embodiment, one of $R^{1A}$ and $R^{1B}$ is H and the other is selected from the group consisting of —$CF_3$ or cyano. In one embodiment, $R^{1A}$ is H and $R^{1B}$ is —$CF_3$. In another embodiment, $R^{1A}$ is —$CF_3$ and $R^{1B}$ is H.

In a further embodiment, $Y_3$ is CH, $Y_2$ is N and $Y_1$ is $CR^{1B}$, one of $R^{1A}$ and $R^{1B}$ is H and the other is selected from the group consisting of F, cyclopropyl, —$CF_3$, or cyano. In one embodiment, one of $R^{1A}$ and $R^{1B}$ is H and the other is selected from the group consisting of F, —$CF_3$, or cyano. In one embodiment, $R^{1A}$ is selected from the group consisting of F, —$CF_3$ or cyano and $R^{1B}$ is H.

In one embodiment, $Y_2$ and $Y_3$ are N and $Y_1$ is $CR^{1B}$, one of $R^{1A}$ and $R^{1B}$ is H and the other is selected from the group consisting of F, cyclopropyl, —$CF_3$, or cyano. In one embodiment, one of $R^{1A}$ and $R^{1B}$ is H and the other is selected from the group consisting of F, —$CF_3$, or cyano. In one embodiment, one of $R^{1A}$ and $R^{1B}$ is H and the other is —$CF_3$. In one embodiment, $R^{1A}$ is —$CF_3$ and $R^{1B}$ is H.

In one embodiment, Z is:

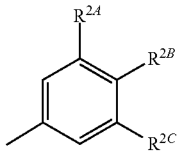

wherein $R^{2A}$, $R^{2B}$ and $R^{2C}$ are as defined herein.

In one embodiment, $R^{2A}$, $R^{2B}$ and $R^{2C}$ are independently selected from the group consisting of H, F, Cl, $CF_3$, cyclopropyl, —(CO)—NH—$CH_3$ and cyano, with the proviso that at least one of $R^{2A}$, $R^{2B}$ and $R^{2C}$ is not H, and with the proviso that only one of $R^{2A}$, $R^{2B}$ and $R^{2C}$ may be —(CO)—NH—$CH_3$ or cyano.

In one embodiment: $R^{2A}$ is selected from the group consisting of H, F, CN and —(CO)—NH—$CH_3$; $R^{2B}$ is selected from the group consisting of H, CN and Cl; and $R^{2C}$ is selected from the group consisting of F and H; with the proviso that at least one of $R^{2A}$, $R^{2B}$ and $R^{2C}$ is not H, and with the proviso that only one of $R^{2A}$, $R^{2B}$ and $R^{2C}$ may be cyano.

In one embodiment: $R^{2A}$ is F or CN, $R^{2B}$ is selected from the group consisting of H and Cl, and $R^{2C}$ is selected from the group consisting of F and H. In a more particular embodiment, $R^{2A}$ is F, $R^{2B}$ is selected from the group consisting of H and Cl, and $R^{2C}$ is selected from the group consisting of F and H. In a more particular embodiment, $R^{2A}$ is F, $R^{2B}$ is selected from the group consisting of H and Cl; and $R^{2C}$ is F. In a more particular embodiment, $R^{2A}$ is F, $R^{2B}$ is Cl, and $R^{2C}$ is F.

In one embodiment, Z is:

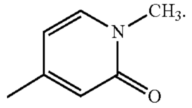

In one embodiment, Z is:

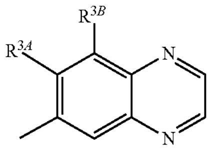

wherein one of $R^{3A}$ and $R^{3B}$ is H and the other is independently selected from the group consisting of F, Cl, Br, $C_{3-6}$cycloalkyl, OR', —N($C_{1-6}$alkyl)$_2$, $C_{2-6}$alkenyl, $C_{2-6}$alkynyl, —(CO)—NH—$CH_3$, cyano and $C_{1-6}$alkyl, wherein said $C_{1-6}$alkyl is optionally substituted with up to 7 fluorine atoms, up to one hydroxy, up to one —N($C_{1-6}$ alkyl)$_2$, and up to one —O$C_{1-6}$alkyl.

In one embodiment, one of $R^{3A}$ and $R^{3B}$ is H and the other is independently selected from the group consisting of F, Cl, $CF_3$. In one embodiment, $R^{3A}$ is H and $R^{3B}$ is independently selected from the group consisting of F, Cl, $CF_3$. In one embodiment, $R^{3A}$ is H and $R^{3B}$ is —$CF_3$. In another embodiment, the present invention relates to compound of Formula I above in which Z is

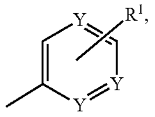 , 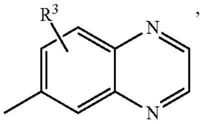

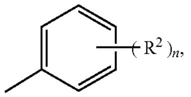 or 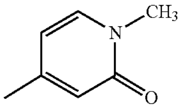 ;

n=1 to 3;

Q is $CF_3$ or $CH_3$;

R is $C_{1-3}$alkyl, phenyl, —$(CH_2)_m$—OH, cyclopropyl, ethynyl, or vinyl;

$R^1$ is cyclopropyl, —$CF_3$, or cyano;

$R^2$ is independently —$CF_3$, —F, —Cl, —Br, cyano, —(CO)—NH—$CH_3$, —$CH_2$—$CH_2$—OH, hydrogen, or cyclopropyl; provided $R^2$ cannot be all hydrogen at the same time;

$R^3$ is —F, —Cl, or —Br;

$R^4$ is H or F;

Y is independently C, CH or N, provided all Y's cannot be CH at the same time; and m is one to three.

In another embodiment, the present invention relates to compound of Formula I above wherein Z is:

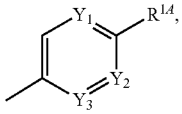 , 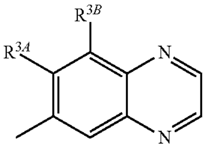 ,

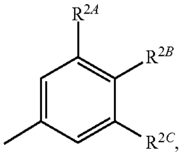 or 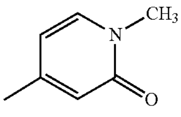 ;

wherein $Y_1$ is N or $CR^{1B}$ and $Y_2$ and $Y_3$ are selected from the group consisting of N or CH, with the proviso that at least one of $Y_1$, $Y_2$ and $Y_3$ is N; and wherein $R^{1A}$, $R^{1B}$, $R^{2A}$, $R^{2B}$, $R^{2C}$, $R^{3A}$ and $R^{3B}$ are independently selected from the group consisting of H, F, Cl, $CF_3$, cyclopropyl, —(CO)—NH—$CH_3$ and cyano, with the provisos that:

where $Y_1$ is $CR^{1B}$, one of $R^{1A}$ and $R^{1B}$ is H;

one of $R^{3A}$ and $R^{3B}$ is H;

at least one of $R^{2A}$, $R^{2B}$ and $R^{2C}$ is not H; and only one of $R^{2A}$, $R^{2B}$ and $R^{2C}$ may be —(CO)—NH—$CH_3$ or cyano; and wherein R is methyl or vinyl; and either Q is $CH_3$ and R4 is H, or Q is $CF_3$ and $R^4$ is H.

In a more particular embodiment, Q is $CH_3$ and $R^4$ is H.

In a more particular embodiment, R is methyl.

In one embodiment the present invention provides a compound which is selected from the group consisting of:

(2R,3S,4R,5S,6R)-2-(Hydroxymethyl)-6-((R)-1-(2-methyl-4-(5-(trifluoromethyl)pyrazin-2-yl)phenyl)ethyl)tetrahydro-2H-pyran-3,4,5-triol;

(2R,3S,4R,5S,6R)-2-(Hydroxymethyl)-6-((R)-1-(2-methyl-4-(4-(trifluoromethyl)pyridin-2-yl)phenyl)ethyl)tetrahydro-2H-pyran-3,4,5-triol;

(2R,3S,4R,5S,6R)-2-(hydroxymethyl)-6-((R)-1-(2-(trifluoromethyl)-4-(5-(trifluoromethyl)pyrazin-2-yl)phenyl)ethyl)tetrahydro-2H-pyran-3,4,5-triol;

(2R,3S,4R,5S,6R)-2-(Hydroxymethyl)-6-((R)-1-(2-methyl-4-(5-(trifluoromethyl)pyridin-3-yl)phenyl)ethyl)tetrahydro-2H-pyran-3,4,5-triol;

(2R,3S,4R,5S,6R)-2-(Hydroxymethyl)-6-((R)-1-(2-methyl-4-(5-(trifluoromethyl)pyrazin-2-yl)phenyl)propyl)tetrahydro-2H-pyran-3,4,5-triol;

(2R,3S,4R,5S,6R)-2-(Hydroxymethyl)-6-((R)-1-(2-methyl-4-(5-(trifluoromethyl)pyrazin-2-yl)phenyl)allyl)tetrahydro-2H-pyran-3,4,5-triol;

(2R,3S,4R,5S,6R)-2-((S)-1-(4'-chloro-3',5'-difluoro-3-methyl-[1,1'-biphenyl]-4-yl)-2-hydroxyethyl)-6-(hydroxymethyl)tetrahydro-2H-pyran-3,4,5-triol;

or a pharmaceutically acceptable salt thereof.

In one embodiment the present invention provides a compound which is (2R,3S,4R,5S,6R)-2-(Hydroxymethyl)-6-((R)-1-(2-methyl-4-(5-(trifluoromethyl)pyrazin-2-yl)phenyl)ethyl)tetrahydro-2H-pyran-3,4,5-triol or a pharmaceutically acceptable salt thereof.

In one embodiment the present invention provides a compound which is (2R,3S,4R,5S,6R)-2-(Hydroxymethyl)-6-((R)-1-(2-methyl-4-(4-(trifluoromethyl)pyridin-2-yl)phenyl)ethyl)tetrahydro-2H-pyran-3,4,5-triol or a pharmaceutically acceptable salt thereof.

In one embodiment the present invention provides a compound which is (2R,3S,4R,5S,6R)-2-(hydroxymethyl)-6-((R)-1-(2-(trifluoromethyl)-4-(5-(trifluoromethyl)pyrazin-2-yl)phenyl)ethyl)tetrahydro-2H-pyran-3,4,5-triol or a pharmaceutically acceptable salt thereof.

In one embodiment the present invention provides a compound which is (2R,3S,4R,5S,6R)-2-(Hydroxymethyl)-6-((R)-1-(2-methyl-4-(5-(trifluoromethyl)pyridin-3-yl)phenyl)ethyl)tetrahydro-2H-pyran-3,4,5-triol or a pharmaceutically acceptable salt thereof.

In one embodiment the present invention provides a compound which is (2R,3S,4R,5S,6R)-2-(Hydroxymethyl)-6-((R)-1-(2-methyl-4-(5-(trifluoromethyl)pyrazin-2-yl)phenyl)propyl)tetrahydro-2H-pyran-3,4,5-triol or a pharmaceutically acceptable salt thereof.

In one embodiment the present invention provides a compound which is (2R,3S,4R,5S,6R)-2-(Hydroxymethyl)-6-((R)-1-(2-methyl-4-(5-(trifluoromethyl)pyrazin-2-yl)phenyl)allyl)tetrahydro-2H-pyran-3,4,5-triol or a pharmaceutically acceptable salt thereof.

In one embodiment the present invention provides a compound which is (2R,3S,4R,5S,6R)-2-((S)-1-(4'-chloro-3',5'-difluoro-3-methyl-[1,1'-biphenyl]-4-yl)-2-hydroxyethyl)-6-(hydroxymethyl)tetrahydro-2H-pyran-3,4,5-triol or a pharmaceutically acceptable salt thereof.

In another embodiment, the present invention provides use as a medicament of a compound of formula I or a pharmaceutically acceptable salt.

In one embodiment, the invention provides a compound of formula I or a pharmaceutically acceptable salt thereof for use in therapy.

In another embodiment, the present invention provides a compound of formula (I) or a pharmaceutically acceptable salt thereof for use in the treatment or prevention of a disease or condition ameliorated by the inhibition of FimH function or activity. In a more particular embodiment, the present invention provides a compound of formula (I) or a pharmaceutically acceptable salt thereof for use in the treatment of a disease or condition ameliorated by the inhibition of FimH function or activity.

In another embodiment, the present invention provides use of a compound of formula (I) or a pharmaceutically acceptable salt thereof in the manufacture of a medicament for the treatment or prevention of a disease or condition ameliorated by the inhibition of FimH function or activity. In a more particular embodiment, the present invention provides use of a compound of formula (I) or a pharmaceutically acceptable salt thereof in the manufacture of a medicament for the treatment of a disease or condition ameliorated by the inhibition of FimH function or activity.

In another embodiment, the present invention provides a method for the treatment of a FimH-mediated disease comprising the administration of a therapeutically effective amount of a compound of formula I or a pharmaceutically acceptable salt to a human patient in need thereof.

In one embodiment, the disease or condition is a bacterial infection, Crohn's disease (CD), or Inflammatory Bowel Disease (IBD) In an embodiment, said bacterial infection is an antibiotic-resistant bacterial infection.

In an embodiment, said disease is Crohn's disease.

In an embodiment, said disease is Inflammatory Bowel Disease.

In an embodiment, said bacterial infection is a urinary tract infection (UTI), including cystitis and pyelonephristis infections.

In an embodiment, said urinary tract infection is recurrent.

In an embodiment, said urinary tract infection is chronic.

In another embodiment, the present invention provides a compound of formula (I) or a pharmaceutically acceptable salt thereof for use in the treatment or prevention of a UTI. In another embodiment, the present invention provides a compound of formula (I) or a pharmaceutically acceptable salt thereof for use in the treatment of a UTI.

In another embodiment, the present invention provides use of a compound of formula I or a pharmaceutically acceptable salt in the manufacture of a medicament for the treatment or prevention of a UTI. In another embodiment, the present invention provides use of a compound of formula I or a pharmaceutically acceptable salt in the manufacture of a medicament for the treatment of a UTI.

In another embodiment, the present invention provides a method for the treatment of urinary tract infection (UTI) comprising the administration of a therapeutically effective amount of a compound of formula I or a pharmaceutically acceptable salt to a human patient in need thereof.

In another embodiment, the present invention provides a pharmaceutical composition comprising a compound of formula I or a pharmaceutically acceptable salt together with a pharmaceutically acceptable carrier.

In an embodiment, said pharmaceutical composition is formulated for oral (PO) administration.

In an embodiment, said pharmaceutical composition is chosen from a tablet and a capsule.

In an embodiment, said pharmaceutical composition is formulated for topical administration.

In another embodiment, the present invention provides a method of treating a FimH-mediated disease comprising the step of administering:

a. a therapeutically effective amount of a compound of formula I or a pharmaceutically acceptable salt thereof, and b. another therapeutic agent.

In another embodiment, the present invention provides a combination of a compound of formula I or a pharmaceutically acceptable salt and another therapeutic agent.

DETAILED DESCRIPTIONS

Definitions

The term "$C_{1-6}$ alkyl," as used herein, alone or in combination, refers to a straight-chain or branched-chain alkyl radical containing from 1 to 6 carbon atoms. Examples of $C_{1-6}$ alkyl radicals include methyl (Me), ethyl (Et), n-propyl, isopropyl, n-butyl, isobutyl, sec-butyl, tert-butyl, pentyl, iso-amyl, hexyl, and the like.

The term "$C_{3-6}$cycloalkyl," as used herein, alone or in combination, refers to a saturated monocyclic alkyl group wherein each cyclic moiety contains from 3 to 6 carbon atom ring members. The examples are cyclopropyl (cPr), cyclopentyl (cPe), cyclobutyl (cBu), and cyclohexyl (cHex).

The term "$C_{2-6}$alkenyl", as used herein, refers to straight or branched hydrocarbon chains containing 2 to 6 carbon atoms, and at least one carbon-carbon double bonds. Examples include ethenyl (or ethylene) and propenyl (or propylene).

The term "$C_{2-6}$alkynyl", as used herein, refers to straight or branched hydrocarbon chains containing 2 to 6 carbon atoms and at least one carbon-carbon triple bonds. Examples include ethynyl (or ethyne) and propynyl (or propyne).

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "optionally substituted" means the anteceding group may be substituted or unsubstituted. When optionally substituted groups are not specifically named, the substituents of an "optionally substituted" group may include one to three substituents independently selected from the following groups or a particular designated set of groups selected from $C_{1-6}$alkyl, $C_{2-6}$alkenyl, $C_{2-6}$alkynyl, —$OC_{1-6}$alkyl, phenyl, cyano, chloro, fluoro, bromo, amido, nitro, —SH, $SCH_3$, —$C(O)CH_3$, —$CO_2H$, aryl or heteroaryl.

Asymmetric centers exist in the compound of formula I. It should be understood, that the present invention covers the compounds of absolute configuration as shown in formula I.

Because of their potential use in medicine, the salts of the compounds of formula I are preferably pharmaceutically acceptable salts. Thus, reference to salts are pharmaceutically acceptable salts. 'Pharmaceutically acceptable' refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. Suitable pharmaceutically acceptable salts include those described by Berge, Bighley and Monkhouse J. Pharm. Sci (1977) 66, pp 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

When a compound of the invention is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, g-hydroxybutyrates, glycollates, tartrates mandelates, and sulfonates, such as xylenesulfonates, methanesulfonates, propanesulfonates, naphthalene-1-sulfonates and naphthalene-2-sulfonates.

If an inventive basic compound is isolated as a salt, the corresponding free base form of that compound may be prepared by any suitable method known to the art, including treatment of the salt with an inorganic or organic base, suitably an inorganic or organic base having a higher pKa than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a sodium salt or a disodium salt.

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing more pure forms used in the pharmaceutical compositions.

The term "combination" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"FimH inhibitor" or "FimH antagonist", is used herein to refer to a compound that exhibits an HAI (hemagglutination inhibition assay) titer or EC>90 with respect to FimH function/activity of no more than about 100 μM and more typically not more than about 50 μM, as measured in the FimH hemagglutination assay (HA) described generally herein. "HAI titer or EC>90" is that concentration of the FimH inhibitor/antagonist which reduces the bacterial agglutination of guinea pig red blood cells by greater than 90%. Certain compounds disclosed herein have been discovered to exhibit inhibition of this FimH function/activity. In certain embodiments, compounds will exhibit an EC>90 with respect to FimH of no more than about 10 μM; in further embodiments, compounds will exhibit an EC>90 with respect to FimH of no more than about 1 μM; in yet further embodiments, compounds will exhibit an EC>90 with respect to FimH of not more than about 250 nM; in yet further embodiments, compounds will exhibit an EC>90 with respect to FimH of not more than about 100 nM in yet further embodiments, compounds will exhibit an EC>90 with respect to FimH of not more than about 50 nM in yet further embodiments, compounds will exhibit an EC>90 with respect to FimH of not more than about 10 nM, as measured in the FimH assay described herein.

The phrase "therapeutically effective" is intended to qualify the amount of active ingredients used in the treatment of a disease or disorder or on the effecting of a clinical endpoint.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

In one embodiment, the term "treat" in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

While it may be possible for the compounds of the subject invention to be administered as the raw chemical, it is also possible to present them as a pharmaceutical formulation (or alternatively referred to as pharmaceutical compositions). Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier (s) must be "therapeutically acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal, inhalation, intranasal, and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

As used herein, the term "compound(s) of the invention" means a compound of formula I in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the rectum, lung, vaginal cavity, ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg. In one embodiment, a compound of the present invention is administered around 150 mg qd (once a day) or bid (twice a day).

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for urinary tract infection involving administration of one of the compounds described herein, increased therapeutic benefit may result by also providing the patient with another therapeutic agent for urinary tract infection. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating FimH-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of FimH-mediated disorders.

Specific diseases to be treated by the compounds, compositions, and methods disclosed herein include bacterial infections, Crohn's Disease, and irritable bowel syndrome (IBS). In certain embodiments, the bacterial infection is a urinary tract infection.

Besides being useful for human treatment, certain compounds and formulations disclosed herein may also be useful for veterinary treatment of companion animals, exotic animals and farm animals, including mammals, and the like. More preferred animals include horses, dogs, and cats.

General Synthetic Schemes for Compounds of the Present Invention

The compounds of the present invention can be made following the synthetic methods or obvious variants thereof described in WO2017/156508. However, without limiting the present invention in any way, the below descriptions also provide reaction methods which can be employed to make compounds of the present invention for the purpose of illustration only. The synthesis of the C-mannoside ketone intermediate followed the route shown in scheme A. The benzyl protected methyl mannoside is allylated with allyl trimethylsilane to form the α-allyl mannoside as the predominant isomer. The terminal double bond is then isomerized to an internal double bond with $(PhCN)_2PdCl_2$. A two-step procedure of dihydroxylation of the double bond and cleavage with sodium periodate produced the aldehyde which is used without further purification (see Wong, C. H et. al. Small Molecules as Structural and Functional Mimics of Sialyl Lewis X in Selectin Inhibition: A Remarkable Enhancement of Inhibition by Additional Negative Charge and/or Hydrophobic Group. J. Amer. Chem. Soc. (1997) 119 (35) 8152-8158). This aldehyde intermediate is reacted with aryl iodide compound A1 and n-butyl lithium species and oxidized with Dess-Martin periodinane to form the ketone A2.

General Synthesis of the Core Mannoside Ketone (Scheme A)

Scheme A

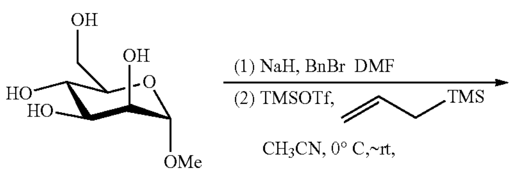

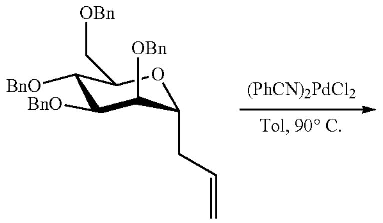

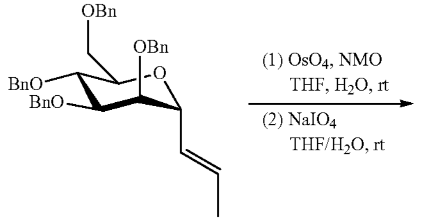

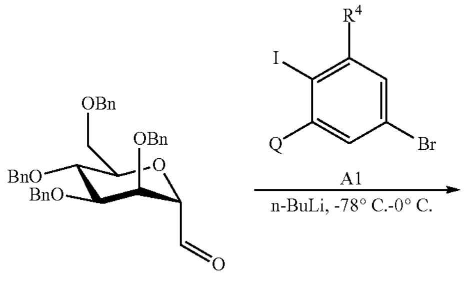

-continued

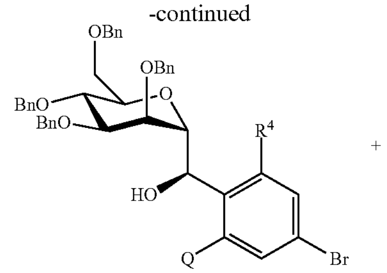

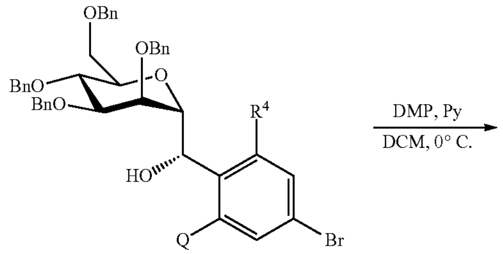

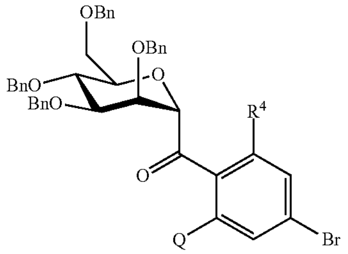

A2

Q = $CH_3$, $CF_3$, Cl
$R^4$ = F, H

The boronate or bromide coupling partners B-E can be synthesized by the schemes shown below. When R is $C_{1-3}$alkyl (optionally substituted with up to 7 fluorine atoms), $C_{2-6}$alkynyl, phenyl, —$(CH_2)_m$—OH, or optionally substituted vinyl, intermediate B can be made by reacting RLi or RMgBr (or R-TMS for cases in which organometallic reagents are not feasible, such as with R=trifluoromethyl) with the ketone A2 followed by reduction of the tertiary alcohol with triethylsilane as illustrated in Scheme B.

Scheme C can alternatively be used in cases where R=methyl if removal of the tertiary alcohol via triethylsilane is problematic, as was found in Example 3 when Q=$CF_3$ and $R^4$=$CF_3$. The organometallic $CH_3MgBr$ was reacted with the ketone A2 followed by elimination of the tertiary alcohol with thionyl chloride. The double bond produced was reduced with Pd on carbon to give intermediate C.

Described in Scheme D is an alternate route to the formation of the benzylic vinyl intermediates D and E, which can be modified to access optionally substituted vinylic derivatives or further derivatized to access R groups comprised of optionally substituted cyclopropyl, hydroxyalkyl, propargyl or alkynyl derivatives. A functionalized phenyl allylsilane is reacted with methyl mannose using a Lewis acid, such as TMS-triflate. The phenyl bromide intermediate D can then be converted to the boronate ester using a palladium catalyst and Bis(pinacolato)diboron to give intermediate E.

Schemes for Synthesis of the Aryl/Heteroaryl Bromide or Boronic Acid Intermediates
Scheme B
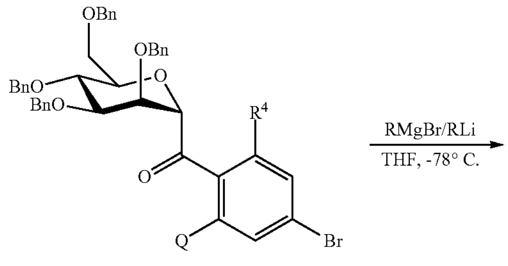
A2
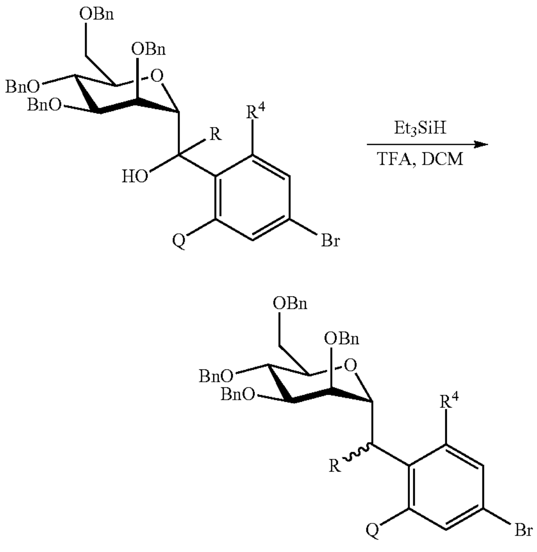
B
Scheme C
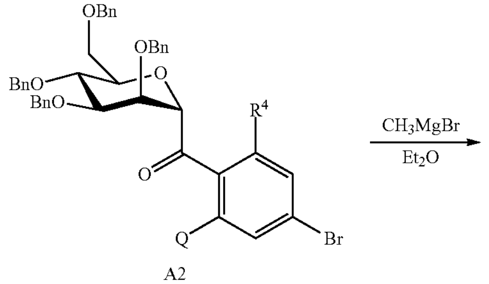
A2
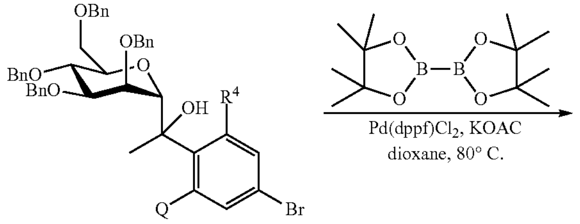
-continued
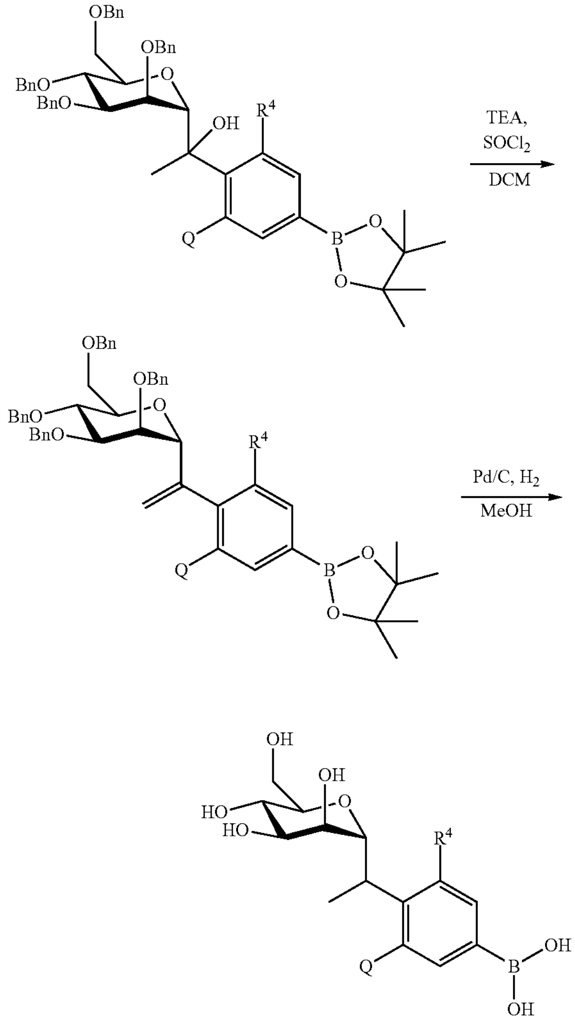
C
Scheme D
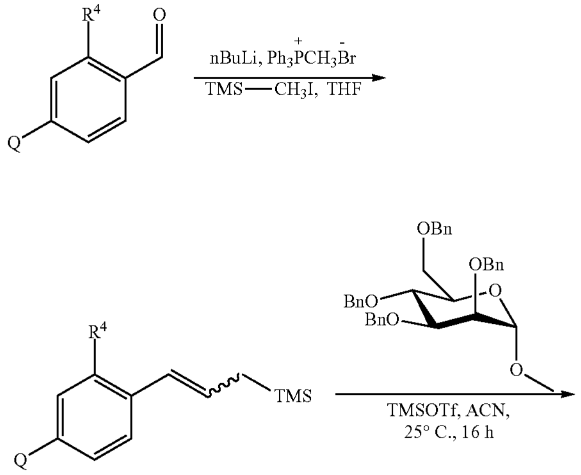

-continued

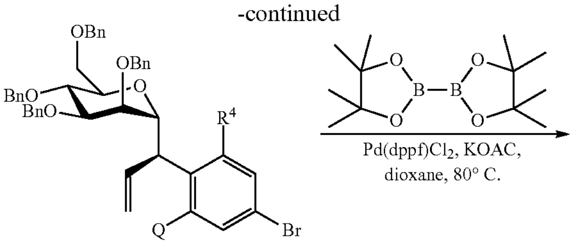

D

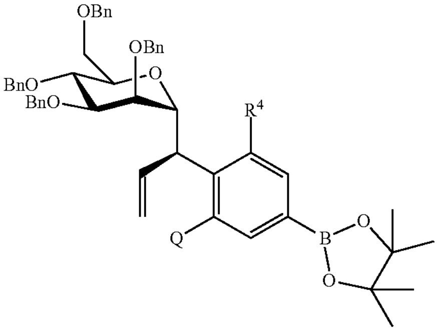

E

Two general schemes for Suzuki coupling are described in Schemes E and F below. All of the examples utilize Suzuki coupling between a halide and boronate. The mannosides are protected with benzyl groups. The benzyl groups can be removed with $BCl_3$ or hydrogenolysis with Pd/C. The R groups can be further functionalized using reactions known in the art. For example, if the R group contains a double bond it can be hydroxylated using hydroboration. Alternately, the double bond can be dihydroxylated with $OsO_4$ and NMO. The diol can be cleaved with $NaIO_4$ to form the aldehyde which can then be reduced with DIBAL.

Two General Schemes for Suzuki Coupling and Deprotection

Scheme E

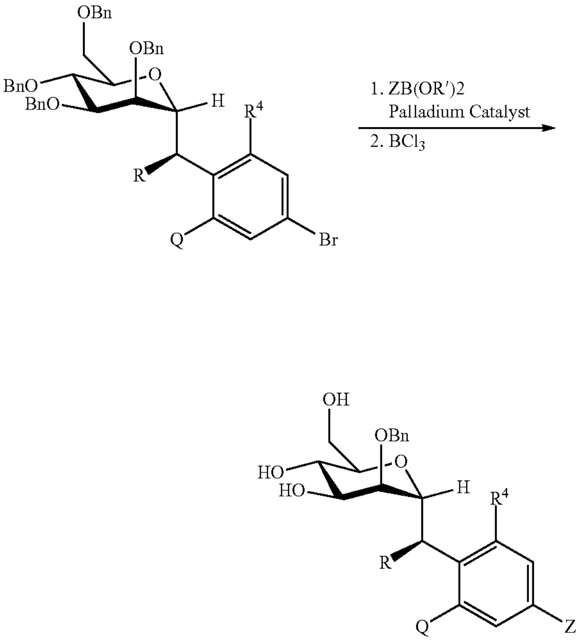

Scheme F

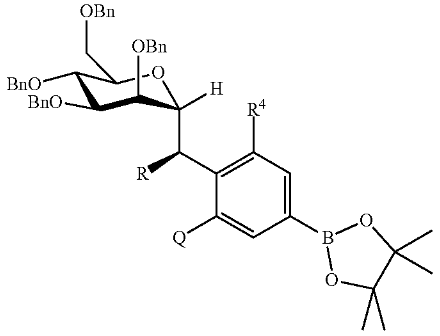

or

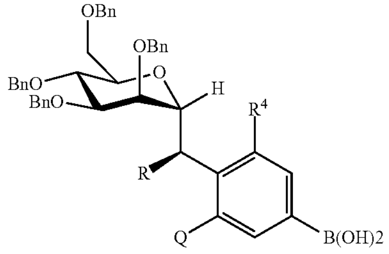

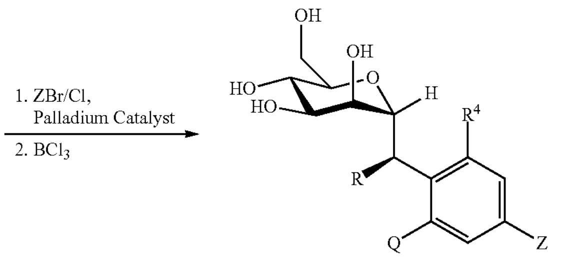

General Procedure for the Suzuki Coupling Reactions:

To a solution of mannoside (1.0 equiv.) in dioxane/water (V/V=5/1) are added aryl boronic acid (or boronate) or aryl halide 0.1 equiv.), cesium carbonate (~3 equiv.) and tetrakis (triphenylphosphine)palladium (~0.05 equiv.) at rt. The resulting mixture is degassed three times. The flask is then placed in an oil bath preheated to 80° C., and allowed to stir for the time specified (typically 30 mi to 2 h). The reaction mixture is then cooled to rt and solvents are evaporated under reduced pressure. The crude residue is then purified by silica gel chromatography. The product is then deprotected by the deprotection protocol.

Deprotection Protocol:

Unless specified otherwise, benzyl ethers are deprotected by adding $BCl_3$ (8.0 equiv, 1M in DCM) to a solution of the partially purified mannoside from the Suzuki reaction in DCM (10 mL) at −78° C. The reaction is stirred for the time specified at −78° C. After completion, the reaction is quenched by MeOH at −78° C. Then the reaction is warmed to rt and concentrated under reduced pressure to afford the debenzylated compound.

Example 1

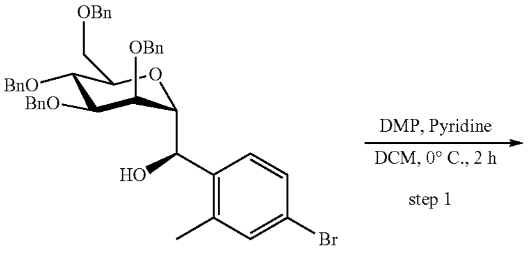

1

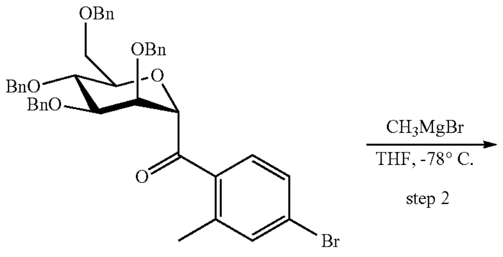

2

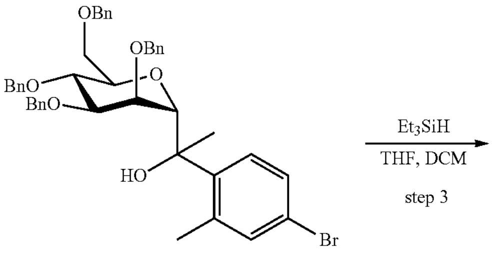

3

-continued

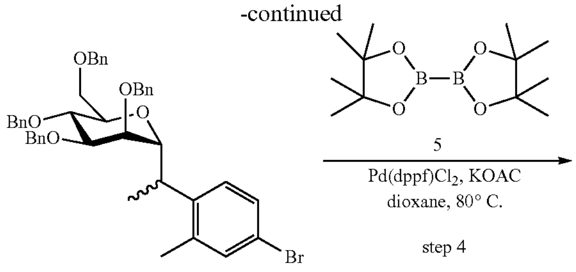

4

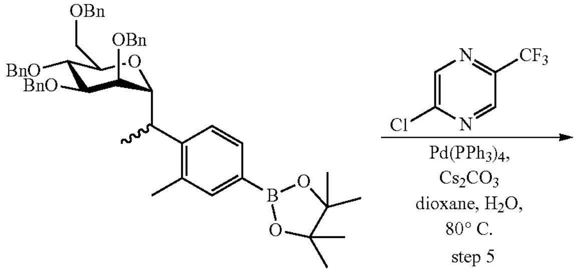

6

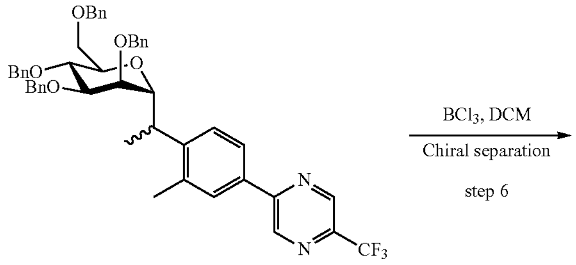

7

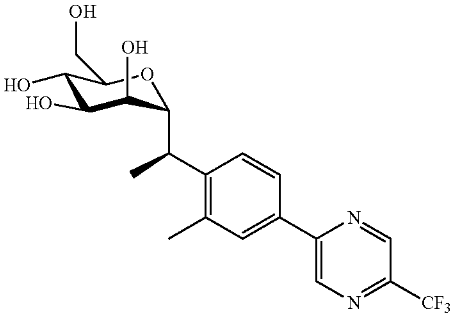

(2R,3S,4R,5S,6R)-2-(hydroxymethyl)-6-((R)-1-(2-methyl-4-(5-(trifluoromethyl)pyrazin-2-yl)phenyl) ethyl)tetrahydro-2H-pyran-3,4,5-triol

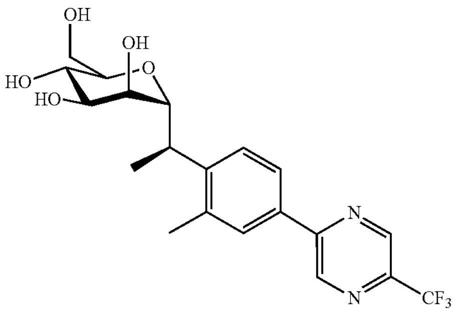

-continued

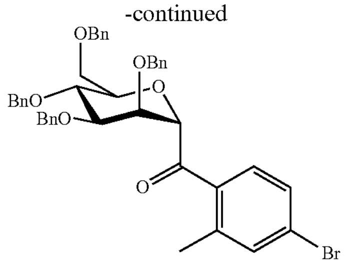

(4-Bromo-2-methylphenyl)((2S,3S,4S,5R,6R)-3,4,5-tris(benzyloxy)-6-((benzyloxy)methyl)tetrahydro-2H-pyran-2-yl)methanone To a solution of (R)-(4-bromo-2-methylphenyl)((2R,3S,4S,5R,6R)-3,4,5-tris(benzyloxy)-6-((benzyloxy)methyl)tetrahydro-2H-pyran-2-yl)methanol (2 g, 2.76 mmol) and pyridine (660 mg, 8.35 mmol) in DCM (20 mL) was added Dess-Martin periodinane (2.34 g, 5.52 mmol) at 0° C. The reaction mixture was stirred for 2 h at 25° C. Upon completion, the reaction was quenched with water (20 mL), extracted with DCM (20 mL×3), the organic phase was combined, washed with brine (20 mL), dried over $MgSO_4$ and concentrated in vacuo to get a residue (2 g) as yellow oil and used to the next step directly without further purification. ESI-MS $[M+Na]^+$ Calc'd for ($C_{42}H_{41}BrO_6$ $Na^+$) 743.22, found, 743.15.

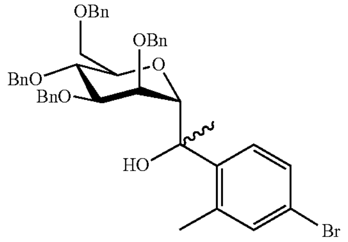

1-(4-bromo-2-methylphenyl)-1-((2S,3S,4S,5R,6R)-3,4,5-tris(benzyloxy)-6-((benzyloxy)methyl)tetrahydro-2H-pyran-2-yl)ethanol To a solution of (4-bromo-2-methylphenyl)((2S,3S,4S,5R,6R)-3,4,5-tris(benzyloxy)-6-((benzyloxy)methyl)tetrahydro-2H-pyran-2-yl)methanone (2 g, 2.77 mmol) in THF (20 mL) was added methylmagnesium bromide (2.8 mL, 8.4 mmol, 3 M in $Et_2O$) at −78° C. The reaction mixture was stirred for 4 h at 25° C. Upon completion, the reaction was quenched with water (20 mL), extracted with ethyl acetate (20 mL×3), the organic phase was combined, washed with brine (20 mL), dried over $Na_2SO_4$ and concentrated in vacuo to get a residue. The residue was purified by column chromatography on silica gel using gradient of 0~25% ethyl acetate in petroleum ether as eluent to afford the title product (2 g, 98% yield) as yellow oil. ESI-MS $[M+H]^+$ Calc'd for ($C_{43}H_{45}BrO_6$ $Na^+$) 759.25, found, 759.15.

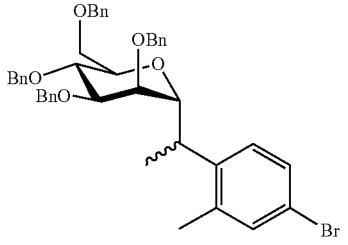

(2R,3R,4R,5R,6R)-3,4,5-Tris(benzyloxy)-2-((benzyloxy)methyl)-6-(1-(4-bromo-2-methylphenyl)ethyl)tetrahydro-2H-pyran To a solution of 1-(4-bromo-2-methylphenyl)-1-((2S,3S,4S,5R,6R)-3,4,5-tris(benzyloxy)-6-((benzyloxy)methyl)tetrahydro-2H-pyran-2-yl)ethanol (2 g, 2.71 mmol) in DCM (30 mL) was added $Et_3SiH$ (1.57 g, 13.5 mmol) and $CF_3COOH$ (3.09 g, 27.1 mmol) at −78° C. The reaction mixture was warmed to 25° C. and stirred for 12 h. Upon completion, the reaction was quenched with water (20 mL), extracted with DCM (20 mL×3), the organic phase was combined, washed with brine (20 mL), dried over $Na_2SO_4$ and concentrated in vacuo to get a residue. The residue was purified by column chromatography on silica gel using gradient of 0~30% ethyl acetate in petroleum ether as eluent to afford the title product (1.8 g, 92% yield) as yellow oil. ESI-MS $[M+Na]^+$ Calc'd for ($C_{43}H_{45}BrO_5$ $Na^+$) 743.25, found, 743.24.

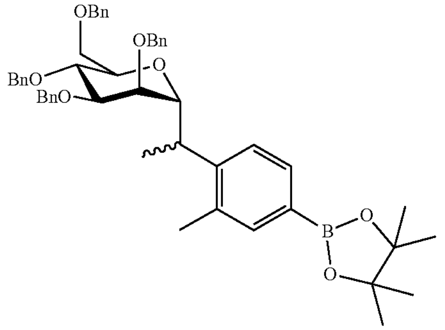

4,4,5,5-Tetramethyl-2-(3-methyl-4-(1-((2R,3R,4R,5R,6R)-3,4,5-tris(benzyloxy)-6-((benzyloxy)methyl)tetrahydro-2H-pyran-2-yl)ethyl)phenyl)-1,3,2-dioxaborolane A mixture of (2R,3R,4R,5R,6R)-3,4,5-tris(benzyloxy)-2-((benzyloxy)methyl)-6-(1-(4-bromo-2-methylphenyl)ethyl)tetrahydro-2H-pyran (1.8 g, 2.5 mmol), 4,4,4',4',5,5,5',5'-octamethyl-2,2'-bi(1,3,2-dioxaborolane) (953 mg, 3.75 mmol), potassium acetate (735 mg, 7.5 mmol) and (1.1'-bis(diphenylphosphino)ferrocene) dichloropalladium(II). $CH_2Cl_2$ (204 mg, 0.25 mmol) in 1,4-dioxane (20 mL) was heated at 80° C. with stirring for 12 h. Upon completion, the reaction was cooled to room temperature and concentrated in vacuo. The residue was purified by column chromatography on silica gel using gradient of 0~30% ethyl acetate in petroleum ether as eluent to afford the title product (1.6 g, 83% yield) as a light brown solid. ESI-MS $[M+Na]^+$ Calc'd for ($C_{49}H_{57}BO_7$ $Na^+$) 791.13, found, 791.16.

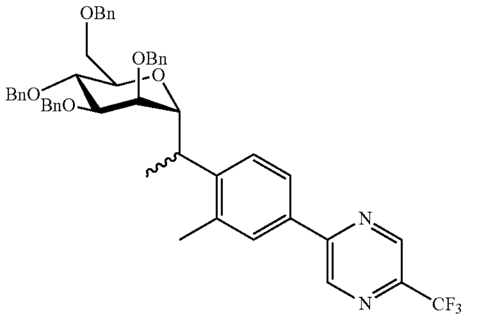

2-(3-Methyl-4-(1-((2R,3R,4R,5R,6R)-3,4,5-tris(benzyloxy)-6-((benzyloxy)methyl)tetrahydro-2H-pyran-2-yl)ethyl)phenyl)-5-(trifluoromethyl)pyrazine A mixture of 4,4,5,5-tetramethyl-2-(3-methyl-4-(1-((2R,3R,4R,5R,6R)-3,4,5-tris(benzyloxy)-6-((benzyloxy)methyl)tetrahydro-2H-pyran-2-yl)ethyl)phenyl)-1,3,2-dioxaborolane (1.6 g, 2.08 mmol), 2-chloro-5-(trifluoromethyl)pyrazine (457 mg, 2.5 mmol), cesium carbonate (2.03 g, 6.25 mmol) and tetrakis(triphenylphosphine)palladium (120 mg, 0.1 mmol) in 1,4-dioxane (15 mL) and water (3 mL) was stirred for 40 min at 80° C. Upon completion, the reaction was quenched with water (20 mL), extracted with ethyl acetate (20 mL×3). The organic phases were combined, washed with brine (20 mL), dried over $Na_2SO_4$ and concentrated in vacuo to get a residue. The residue was purified by column chromatography on silica gel using gradient of 0-17% ethyl acetate in petroleum ether as eluent to afford the title product (1.4 g, 85% yield) as yellow oil. ESI-MS $[M+Na]^+$ Calc'd for ($C_{48}H_{47}F_3N_2O_5$ $Na^+$) 811.34, found, 811.16.

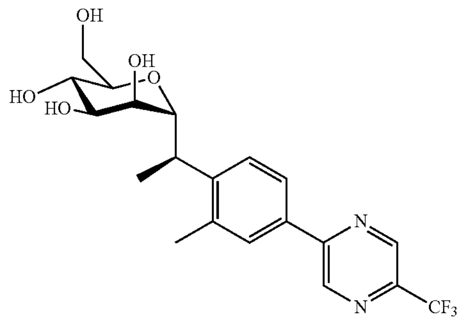

(2R,3S,4R,5S,6R)-2-(Hydroxymethyl)-6-((R)-1-(2-methyl-4-(5-(trifluoromethyl)pyrazin-2-yl)phenyl)ethyl)tetrahydro-2H-pyran-3,4,5-triol To a solution of 2-(3-methyl-4-(1-((2R,3R,4R,5R,6R)-3,4,5-tris(benzyloxy)-6-((benzyloxy)methyl)tetrahydro-2H-pyran-2-yl)ethyl)phenyl)-5-(trifluoromethyl)pyrazine (1.4 g, 1.78 mmol) in DCM (20 mL) was dropwise added $BCl_3$ (1N in DCM, 14.2 mL, 14.2 mmol) at −78° C. The resulting solution was stirred for 40 min at −78° C. Upon completion, the reaction was quenched by MeOH (12 mL) and concentrated under reduced pressure to get a residue. The residue was purified by Prep-HPLC with conditions: Column: XBridge Prep OBD C18 Column 30×150 mm 5um; Mobile Phase A: Water (10 mmol/L $NH_4HCO_3$), Mobile Phase B: ACN; Flow rate: 60 mL/min; Gradient: 25% B to 45% B in 9 min; 220 nm; Rt: 7.82 min; Injection Volume: 2 ml; Number Of Runs: 3; to afford mixture (300 mg). The mixture was further separated with Prep-Chiral with conditions: Column: CHIRALPAK IF, 2*25 cm, 5 um; Mobile Phase A:Hex (8 mmol/L $NH_3$.MeOH)-HPLC, Mobile Phase B: EtOH-HPLC; Flow rate: 20 mL/min; Gradient: 30 B to 30 B in 18 min; 254/220 nm; Injection Volume: 1 ml; Number Of Runs: 12; Fraction at RT=9.25 min with MS signal of the desired product were collected and concentrated in vacuo to afford the title product (200 mg, 26% yield) as a white solid. Formula: $C_{20}H_{23}F_3N_2O_5$ Exact Mass: 428.16 Molecular Weight: 428.41.

Analytical data: $^1H$ NMR (300 MHz, Methanol-$d_4$) δ 9.28 (d, J=1.5 Hz, 1H), 9.08-8.99 (m, 1H), 8.02-8.00 (m, 2H), 7.57 (d, J=8.9 Hz, 1H), 4.24 (dd, J=10.1 Hz, 2.7 Hz, 1H), 4.10 (t, J=3.0 Hz, 1H), 3.82 (dd, J=8.6 Hz, 3.2 Hz, 1H), 3.73 (t, J=8.5 Hz, 1H), 3.58-3.51 (m, 2H), 3.40 (dd, J=11.7 Hz, 2.9 Hz, 1H), 3.24-3.19 (m, 1H), 2.52 (s, 3H), 1.29 (d, J=6.8 Hz, 3H). ESI-MS $[M+Na]^+$ Calc'd for ($C_{20}H_{23}F_3N_2O_5Na^+$) 451.15, found, 451.10.

Example 2

(2R,3S,4R,5S,6R)-2-(Hydroxymethyl)-6-((R)-1-(2-methyl-4-(4-(trifluoromethyl)pyridin-2-yl)phenyl)ethyl)tetrahydro-2H-pyran-3,4,5-triol

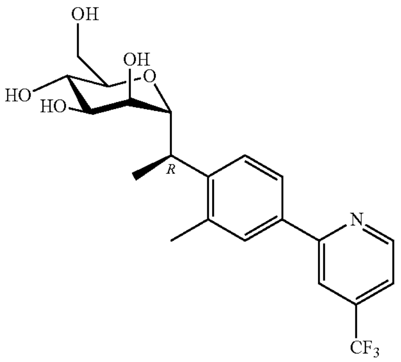

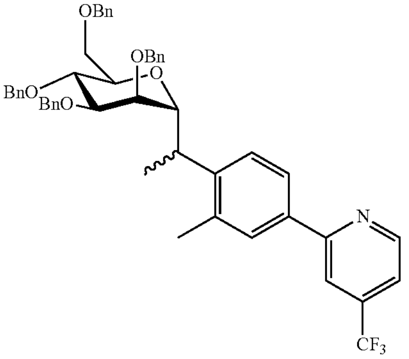

2-(3-Methyl-4-(1-((2R,3R,4R,5R,6R)-3,4,5-tris(benzyloxy)-6-((benzyloxy)methyl)tetrahydro-2H-pyran-2-yl)ethyl)phenyl)-4-(trifluoromethyl)pyridine To a solution of 4,4,5,5-tetramethyl-2-(3-methyl-4-(1-((2R,3R,4R,5R,6R)-3,4,5-tris(benzyloxy)-6-((benzyloxy)

methyl)tetrahydro-2H-pyran-2-yl)ethyl)phenyl)-1,3,2-dioxaborolane (800 mg, 1.041 mmol) in 1,4-dioxane (8 mL) and water (2.0 mL) were added 2-chloro-4-(trifluoromethyl) pyridine (189 mg, 1.041 mmol), tetrakis(triphenylphosphine)palladium(0) (120 mg, 0.104 mmol), $Cs_2CO_3$ (678 mg, 2.081 mmol). The resulting solution was stirred for 1.5 h at 80° C. The reaction mixture was cooled to room temperature, quenched with water (10 mL), extracted with ethyl acetate (10 mL×3), dried over $Na_2SO_4$ and filtered. The filtrate was concentrated to give a residue. The residue was purified by column chromatography on silica gel using gradient of 0~18% ethyl acetate in petroleum ether. Fraction with MS signal of desired product were combined and concentrate under vacuum to give title product (630 mg, 0.8 mmol, 77% yield) as yellow oil. ESI-MS $[M+Na]^+$ Calc'd for ($C_{49}H_{48}F_3N_2O_5$ $Na^+$) 810.34, found, 810.0.

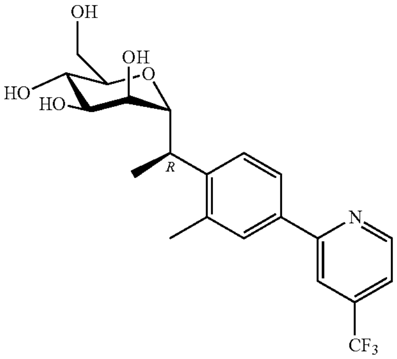

(2R,3S,4R,5S,6R)-2-(Hydroxymethyl)-6-((R)-1-(2-methyl-4-(4-(trifluoromethyl)pyridin-2-yl)phenyl) ethyl)tetrahydro-2H-pyran-3,4,5-triol and (2R,3S,4R,5S,6R)-2-(Hydroxymethyl)-6-((S)-1-(2-methyl-4-(4-(trifluoromethyl)pyridin-2-yl)phenyl)ethyl) tetrahydro-2H-pyran-3,4,5-triol To a solution of 2-(3-methyl-4-(1-((2R,3R,4R,5R,6R)-3,4,5-tris(benzyloxy)-6-((benzyloxy)methyl)tetrahydro-2H-pyran-2-yl)ethyl)phenyl)-4-(trifluoromethyl)pyridine (630 mg, 0.800 mmol) in DCM (10 mL) at −78° C., was added $BCl_3$ (1N in DCM, 6.40 mL, 6.40 mmol) under $N_2$. The reaction mixture was stirred at −78° C. for 1 h under $N_2$. The reaction mixture was quenched with MeOH (5 mL) and concentrated by rotary evaporator to get a residue. The residue was purified by Prep-HPLC with conditions: Column: XBridge Shield RP18 OBD Column 30*150 mm, 5 um; Mobile Phase A: Water (10 mmol/L $NH_4HCO_3$), Mobile Phase B: ACN; Flow rate: 60 mL/min; Gradient: 23% B to 43% B in 7 min; 254 nm; Rt: 6.77 min; Injection Volume: 1.40 ml; Number Of Runs:5 to afford the mixture (190 mg mixture of two isomers) as white solid. The mixture was further separated by chiral-HPLC with conditions: Column: CHIRALPAK IG, 20*250 mm, 5 um; Mobile Phase A: Hex (8 mmol/L NH3.MeOH)-HPLC, Mobile Phase B: EtOH-HPLC; Flow rate: 20 mL/min; Gradient: 25 B to 25 B in 16 min; 220/254 nm; RT1:10.423 min; RT2:12.47 min; Injection Volume: 0.5 ml; Number of Runs: 14;

The faster-eluting isomer fractions was collected and concentrated under reduced pressure to afford (2R,3S,4R,5S,6R)-2-(hydroxymethyl)-6-((R)-1-(2-methyl-4-(4-(trifluoromethyl)pyridin-2-yl)phenyl)ethyl)tetrahydro-2H-pyran-3,4,5-triol (88 mg, 25.8% yield, R isomer, assumed) as a white solid.

Formula: $C_{21}H_{24}F_3NO_5$ Exact Mass: 427.16 Molecular Weight: 427.42.

Analytical data: $^1H$ NMR (400 MHz, Methanol-$d_4$) δ 8.85 (d, J=5.1 Hz, 1H), 8.09 (s, 1H), 7.87-7.86 (m, 2H), 7.60 (d, J=5.1 Hz, 1H), 7.52 (d, J=8.6 Hz, 1H), 4.23 (dd, J=10.2 Hz, 2.6 Hz, 1H), 4.11 (t, J=2.9 Hz, 1H), 3.82 (dd, J=8.6 Hz, 3.2 Hz, 1H), 3.72 (t, J=8.6 Hz, 1H), 3.56-3.52 (m, 2H), 3.40 (dd, J=11.6 Hz, 2.8 Hz, 1H), 3.23-3.19 (m, 1H), 2.52 (s, 3H), 1.29 (d, J=6.8 Hz, 3H). ESI-MS $[M+Na]^+$ Calc'd for ($C_{21}H_{24}F_3NO_5$ $Na^+$) 450.15, found, 450.10.

The slower-eluting isomer fractions was collected and concentrated under reduced pressure to afford (2R,3S,4R,5S,6R)-2-(hydroxymethyl)-6-((S)-1-(2-methyl-4-(4-(trifluoromethyl)pyridin-2-yl)phenyl)ethyl)tetrahydro-2H-pyran-3,4,5-triol (7 mg, 2.05% yield, S isomer, assumed) as a white solid.

Formula: $C_{21}H_{24}F_3NO_5$ Exact Mass: 427.16 Molecular Weight: 427.42.

Analytical data: $^1H$ NMR (400 MHz, Methanol-$d_4$) δ 8.87 (d, J=5.2 Hz, 1H), 8.11 (s, 1H), 7.93-7.92 (m, 2H), 7.60 (d, J=5.4 Hz, 1H), 7.46 (d, J=8.0 Hz, 1H), 4.14-4.05 (dd, J=11.4 Hz, 2.6 Hz, 1H), 3.91 (dd, J=11.8 Hz, 2.4 Hz, 1H), 3.78-3.72 (m, 2H), 3.69-3.49 (m, 4H), 2.52 (s, 3H), 1.35 (d, J=6.8 Hz, 3H). ESI-MS $[M+H]^+$ Calc'd for ($C_{21}H_{24}F_3NO_5H^+$) 428.17, found, 428.15.

Example 3

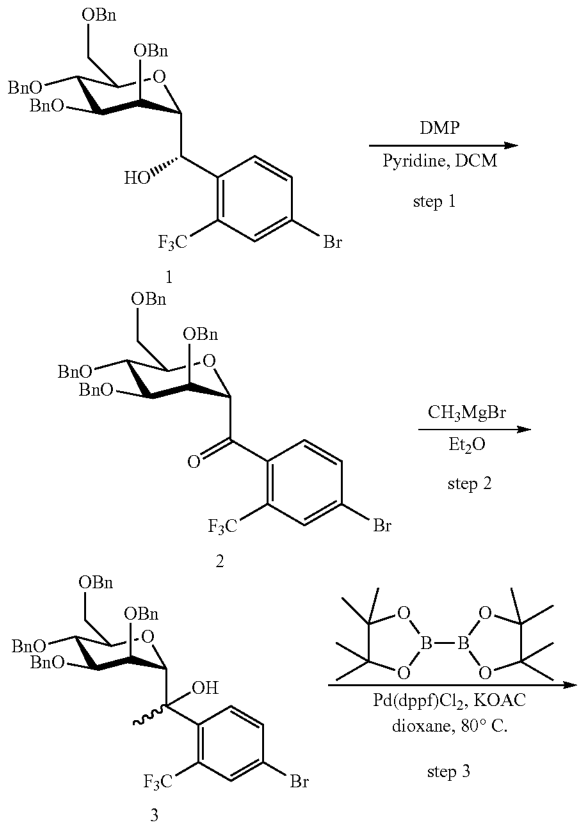

-continued

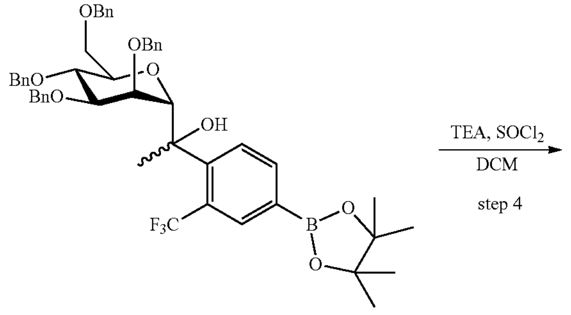

4

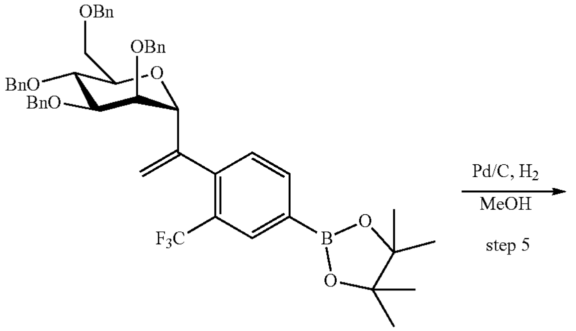

5

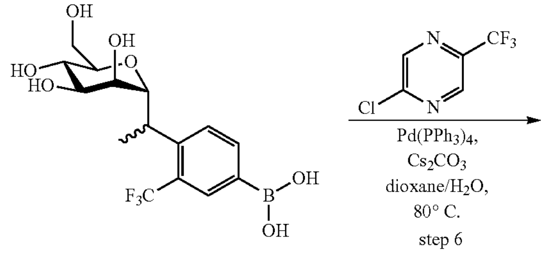

6

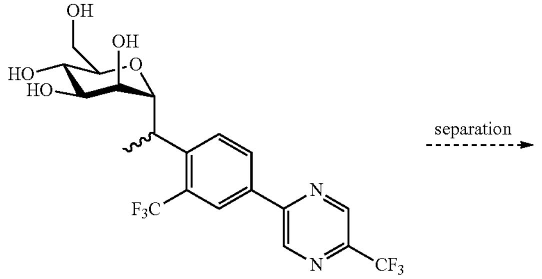

7

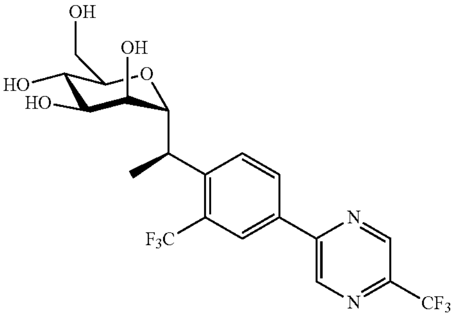

PH-CSX-51982-001-666

(2R,3S,4R,5S,6R)-2-(Hydroxymethyl)-6-((R)-1-(2-(trifluoromethyl)-4-(5-(trifluoromethyl)pyrazin-2-yl)phenyl)ethyl)tetrahydro-2H-pyran-3,4,5-triol

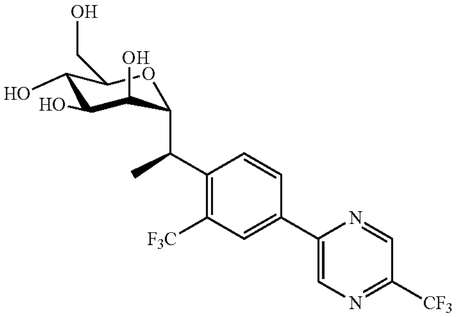

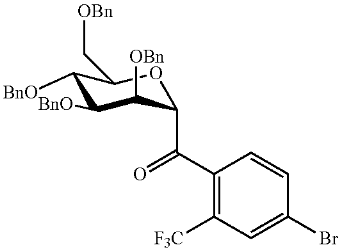

(4-bromo-2-(trifluoromethyl)phenyl)((2S,3S,4S,5R,6R)-3,4,5-tris(benzyloxy)-6-((benzyloxy)methyl)tetrahydro-2H-pyran-2-yl)methanone To a solution of (S)-(4-bromo-2-(trifluoromethyl)phenyl)((2R,3S,4S,5R,6R)-3,4,5-tris(benzyloxy)-6-((benzyloxy)methyl)tetrahydro-2H-pyran-2-yl)methanol (5.45 g, 7.01 mmol) in DCM (50 mL) was added pyridine (1.700 mL, 21.02 mmol), Dess-Martin periodinane (5.94 g, 14.02 mmol) at 0° C. Then the reaction mixture was stirred at 0° C. for 2 h. A sample was taken from the reaction mixture and diluted with MeOH and submitted for LCMS analysis and it showed the reaction was complete. The reaction mixture was quenched with 10% $Na_2S_2O_3$(aq) (50 mL)/saturated $NaHCO_3$ (aq) (50 mL) and then extracted with DCM (10 mL×3). The organic layers were combined, washed with saturated $NaHCO_3$ (aq) (100 mL), dried over $MgSO_4$ and filtered. The filtrate was concentrated to get 4-bromo-2-(trifluoromethyl)phenyl)((2S,3S,4S,5R,6R)-3,4,5-tris(benzyloxy)-6-((benzyloxy)methyl) tetrahydro-2H-pyran-2-yl) methanone (5.3 g, 6.83 mmol, 98% yield) (orange oil) which was taken forward for next step without further purification. ESI-MS $[M+Na]^+$ Calc'd for ($C_{42}H_{38}BrF_3O_6Na^+$) 797.17, found, 797.

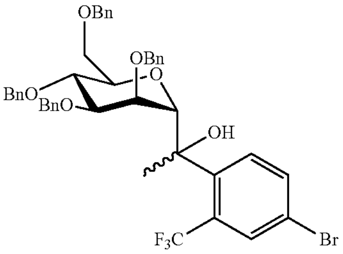

1-(4-Bromo-2-(trifluoromethyl)phenyl)-1-((2S,3S,4S,5R,6R)-3,4,5-tris(benzyloxy)-6-((benzyloxy)methyl)tetrahydro-2H-pyran-2-yl)ethan-1-ol To a solution of (4-bromo-2-(trifluoromethyl)phenyl)((2S,3S,4S,5R,6R)-3,4,5-tris(benzyloxy)-6-((benzyloxy)methyl)tetrahydro-2H-pyran-2-yl)methanone (5.3 g, 6.83 mmol) in tetrahydrofuran (THF) (50 mL) was added methylmagnesium bromide (34.2 mL, 34.2 mmol) at −78° C. Then the reaction mixture was warmed to 25° C. and stirred for 12 hr. A sample was taken from the reaction mixture and diluted with MeOH and submitted for LCMS analysis which showed the reaction was complete. The reaction mixture was quenched with water (50 mL) and then extracted with ethyl acetate (50 mL×3). The organic layers were combined, washed with water (50 mL), dried over $Na_2SO_4$ and filtered. The filtrate was concentrated to get a residue. The residue was dissolved with DCM (40 mL), pre-adsorbed by evaporation onto silica gel then purified by silica gel chromatography, eluting with EtOAc in petroleum ether (17%). Fractions with MS signal of desired product were collected and concentrated in vacuo to afford 1-(4-bromo-2-(trifluoromethyl)phenyl)-1-((2S,3S,4S,5R,6R)-3,4,5-tris(benzyloxy)-6-((benzyloxy)methyl)tetrahydro-2H-pyran-2-yl)ethan-1-ol (4.8 g, 5.68 mmol, 83% yield) as an orange oil. ESI-MS $[M+Na]^+$ Calc'd for $(C_{43}H_{42}BrF_3O_6Na^+)$ 813.20, found, 813.

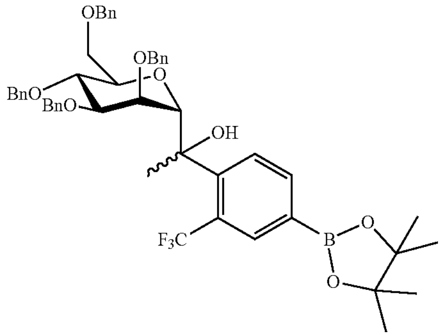

1-(4-(4,4,5,5-tetramethyl-1,3,2-dioxaborolan-2-yl)-2-(trifluoromethyl)phenyl)-1-((2S,3S,4S,5R,6R)-3,4,5-tris(benzyloxy)-6-((benzyloxy)methyl)tetrahydro-2H-pyran-2-yl)ethan-1-ol To a solution of 1-(4-bromo-2-(trifluoromethyl)phenyl)-1-((2S,3S,4S,5R,6R)-3,4,5-tris(benzyloxy)-6-((benzyloxy)methyl)tetrahydro-2H-pyran-2-yl)ethan-1-ol (3.8 g, 4.80 mmol), 4,4,4',4',5,5,5',5'-octamethyl-2,2'-bi(1,3,2-dioxaborolane) (1.463 g, 5.76 mmol) and potassium acetate (1.413 g, 14.40 mmol) in 1,4-dioxane (40 mL) was added $PdCl_2(dppf)$-$CH_2Cl_2$ adduct (0.392 g, 0.480 mmol). The reaction mixture was stirred at 80° C. for 16 h then LCMS analysis showed that the reaction was complete. The reaction mixture was cooled to room temperature. The reaction mixture was quenched with water (50 mL) and extracted with ethyl acetate (40 mL×3). The combined organic phase was washed with brine (40 mL) and dried over $Na_2SO_4$. The mixture was filtered and the filtrate was concentrated under vacuum to get a residue. The residue was dissolved in ethyl acetate and pre-adsorbed by evaporation onto silica gel (4 gram) then purified by column chromatography on silica gel using gradient of 0-20% ethyl acetate in petroleum ether as eluent to afford the title product. Fractions with the same MS signal was collected and concentrated to give product 1-(4-(4,4,5,5-tetramethyl-1,3,2-dioxaborolan-2-yl)-2-(trifluoromethyl)phenyl)-1-((2S,3S,4S,5R,6R)-3,4,5-tris(benzyloxy)-6-((benzyloxy)methyl)tetrahydro-2H-pyran-2-yl)ethan-1-ol (3.80 g, 4.00 mmol, 83% yield) as an orange oil. ESI-MS $[M+Na]^+$ Calc'd for $(C_{49}H_{54}BF_3O_8Na^+)$ 861.38, found 861.

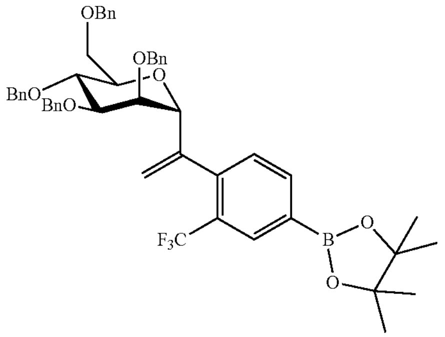

4,4,5,5-tetramethyl-2-(3-(trifluoromethyl)-4-(1-((2R,3R,4R,5R,6R)-3,4,5-tris(benzyloxy)-6-((benzyloxy)methyl)tetrahydro-2H-pyran-2-yl)vinyl)phenyl)-1,3,2-dioxaborolane To a solution of 1-(4-(4,4,5,5-tetramethyl-1,3,2-dioxaborolan-2-yl)-2-(trifluoromethyl)phenyl)-1-((2S,3S,4S,5R,6R)-3,4,5-tris(benzyloxy)-6-((benzyloxy)methyl)tetrahydro-2H-pyran-2-yl)ethan-1-ol (3.2 g, 3.82 mmol) and TEA (2.127 mL, 15.26 mmol) in DCM (30 mL) was added $SOCl_2$ (0.557 mL, 7.63 mmol) dropwise at 0° C. The reaction was stirred at 0° C. for 30 min when a LCMS was taken showing that the reaction was complete. The reaction was quenched with water (30 mL), and extracted with DCM (3×50 mL). The combined organic layers were washed with water (50 mL), dried over $Na_2SO_4$ and filtered. The filtrate was concentrated under reduced pressure to get a crude product (3.2 g, brown oil). The residue was dissolved with DCM (50 mL), pre-adsorbed by evaporation onto silica gel (7 g) and loaded onto the column then purified by silica gel chromatography, eluting with EtOAc in petroleum (17%). Fractions with MS signal of desired product were collected and concentrated in vacuo to afford 4,4,5,5-tetramethyl-2-(3-(trifluoromethyl)-4-(1-((2R,3R,4R,5R,6R)-3,4,5-tris(benzyloxy)-6-((benzyloxy)methyl)tetrahydro-2H-pyran-2-yl)vinyl)phenyl)-1,3,2-dioxaborolane (2.5 g, 62.4% yield, partially hydrolyzed to boronic acid) as an orange oil. ESI-MS $[M+Na]^+$ Calc'd for $(C_{49}H_{52}BF_3O_7Na^+)$ 843.37, found 843.

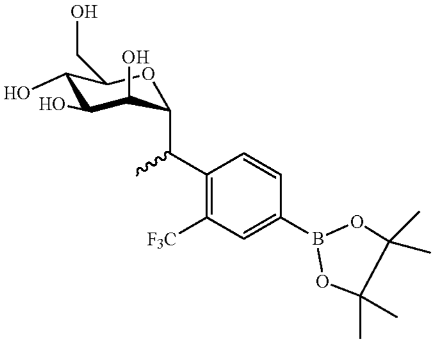

(2R,3S,4R,5S,6R)-2-(hydroxymethyl)-6-(1-(4-(4,4,5,5-tetramethyl-1,3,2-dioxaborolan-2-yl)-2-(trifluoromethyl)phenyl)ethyl)tetrahydro-2H-pyran-3,4,5-triol A mixture of 4,4,5,5-tetramethyl-2-(3-(trifluoromethyl)-4-(1-((2R,3R,4R,5R,6R)-3,4,5-tris(benzyloxy)-6-((benzyloxy)methyl)tetrahydro-2H-pyran-2-yl)vinyl)phenyl)-1,3,2-dioxaborolane (2.4 g, 2.92 mmol) and palladium on carbon (1.5 g, 1.410 mmol) in MeOH (15 mL) was stirred at 25° C. The resulting mixture was degassed three times with hydrogen and then stirred for 11 h under hydrogen (~3 atm) at 25° C. The reaction was monitored by LCMS. LCMS showed the benzyl groups were removed but the double bond still existed. The reaction was stopped and re-subjected to the reaction conditions for an additional 12 h. LCMS showed that the reaction was complete. The reaction mixture was filtered through celite and the filter cake was washed with MeOH (10 ml). The filtrate was concentrated under reduced pressure to afford the title product (2R,3S,4R,5S,6R)-2-(hydroxymethyl)-6-(1-(4-(4,4,5,5-tetramethyl-1,3,2-dioxaborolan-2-yl)-2-(trifluoromethyl)phenyl)ethyl)tetrahydro-2H-pyran-3,4,5-triol (1.1 g, 1.071 mmol, 36.6% yield) as a colorless oil. ESI-MS $[M+Na]^+$ Calc'd for $(C_{21}H_{30}BF_3O_7Na^+)$ 485.19, found, 485.

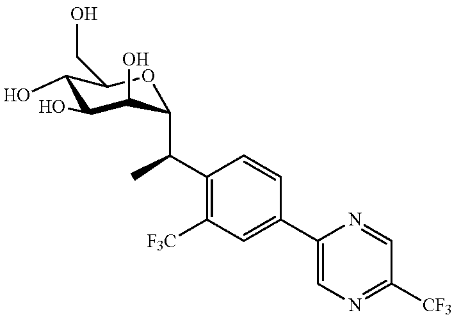

(2R,3S,4R,5S,6R)-2-(hydroxymethyl)-6-((R)-1-(2-(trifluoromethyl)-4-(5-(trifluoromethyl)pyrazin-2-yl)phenyl)ethyl)tetrahydro-2H-pyran-3,4,5-triol To a solution of (2R,3S,4R,5S,6R)-2-(hydroxymethyl)-6-(1-(4-(4,4,5,5-tetramethyl-1,3,2-dioxaborolan-2-yl)-2-(trifluoromethyl)phenyl)ethyl)tetrahydro-2H-pyran-3,4,5-triol (600 mg, 1.298 mmol) and 2-chloro-5-(trifluoromethyl)pyrazine (284 mg, 1.558 mmol) in 1,4-dioxane (10 mL) and water (2 mL) were added $Pd(Ph_3P)_4$ (150 mg, 0.130 mmol) and $Cs_2CO_3$ (1269 mg, 3.89 mmol) at 25° C. The reaction mixture was stirred at 80° C. for 2 h. A sample was taken from the reaction mixture directly and diluted with MeOH, then submitted for LC-MS analysis. The LC-MS showed that the starting material was consumed completely. The reaction mixture was cooled to room temperature. The reaction mixture was quenched with water (10 mL), and then extracted with ethyl acetate (3×10 mL). The organic layers were combined, washed with water (10 mL), dried over $Na_2SO_4$ and filtered. The filtrate was concentrated to get a residue. The residue was dissolved in MeOH (3 mL), then purified by TLC, to get a residue (350 mg), as a yellow solid. Then the solid was purified by Prep-chiral HPLC, Column: Lux 5 um Cellulose-4, 5*25 cm, 5 um; Mobile Phase A:, Mobile Phase B:; Flow rate:150 mL/min; Gradient:0 B to 0 B in min; 220 nm; RT1:6.5; RT2:8.1; Injection Volume:4 ml; Number Of Runs:10; to (2R,3S,4R,5S,6R)-2-(hydroxymethyl)-6-((R)-1-(2-(trifluoromethyl)-4-(5-(trifluoromethyl)pyrazin-2-yl)phenyl)ethyl)tetrahydro-2H-pyran-3,4,5-triol (73 mg, 0.150 mmol, 11.54% yield) as a white solid. Formula: $C_{20}H_{20}F_6N_2O_5$. Exact Mass: 482.13, Molecular Weight: 482.38.

Analytical Data: 1H NMR (400 MHz, CD3OD) δ ppm: 9.36 (s, 1H), 9.09 (s, 1H), 8.52 (s, 1H), 8.42 (d, J=10 Hz, 1H), 7.88 (d, J=8.4 Hz, 1H), 4.30 (d, J=10 Hz, 1H), 4.10-4.11 (m, 1H), 3.61-3.75 (m, 3H), 3.47-3.53 (m, 1H), 3.34 (d, J=2.8 Hz, 1H), 3.12-3.20 (m, 1H), 1.33 (d, J=6.4 Hz, 3H). ESI-MS $[M+H]^+$ Calc'd for $(C_{20}H_{20}F_6N_2O_5H^+)$ 483.14, found, 483.14.

Example 4

(2R,3S,4R,5S,6R)-2-(Hydroxymethyl)-6-((R)-1-(2-methyl-4-(5-(trifluoromethyl)pyridin-3-yl)phenyl)ethyl)tetrahydro-2H-pyran-3,4,5-triol

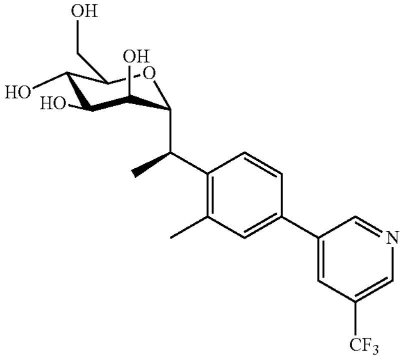

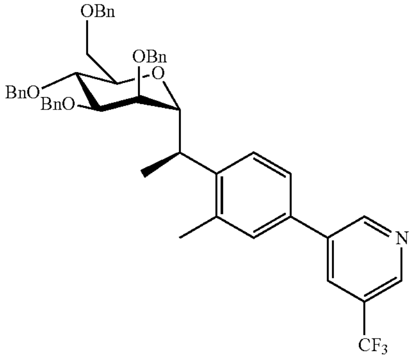

3-(3-Methyl-4-((R)-1-((2R,3R,4R,5R,6R)-3,4,5-tris(benzyloxy)-6-((benzyloxy)methyl)tetrahydro-2H-pyran-2-yl)ethyl)phenyl)-5-(trifluoromethyl)pyridine To a solution of 4,4,5,5-tetramethyl-2-(3-methyl-4-((R)-1-((2R,3R,4R,5R,6R)-3,4,5-tris(benzyloxy)-6-((benzyloxy)methyl)tetrahydro-2H-pyran-2-yl)ethyl)phenyl)-1,3,2-dioxaborolane (150 mg, 0.195 mmol) in water (1 mL) and 1,4-dioxane (4.0 mL) were added 3-bromo-5-(trifluoromethyl)pyridine (44.1 mg, 0.195 mmol), tetrakis(triphenylphosphine)palladium(0) (22.55 mg, 0.020 mmol) and $Cs_2CO_3$ (127 mg, 0.390 mmol) at 25° C. The reaction mixture was stirred at 80° C. for 40 min. The reaction mixture was cooled to room temperature, quenched with water (5 mL), extracted with ethyl acetate (5 mL×3), dried over $Na_2SO_4$ and filtered. The filtrate was concentrated to give a residue. The residue was dissolved in DCM (5 mL), then purified by Prep-TLC (ethyl acetate-petroleum ether=1:4). Bands with Rf=0.5 were combined, washed with ethyl acetate. The appropriate fractions were combined and concentrated under vacuum to give the the title compound (110 mg, 72% yield) as a yellow oil. ESI-MS $[M+H]^+$ Calc'd for $(C_{49}H_{48}F_3NO_5H^+)$ 788.36, found, 788.0.

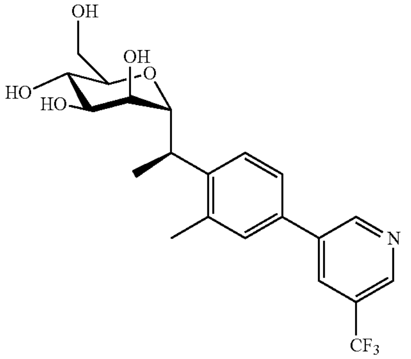

(2R,3S,4R,5S,6R)-2-(Hydroxymethyl)-6-((R)-1-(2-methyl-4-(5-(trifluoromethyl)pyridin-3-yl)phenyl)ethyl)tetrahydro-2H-pyran-3,4,5-triol To a solution of 3-(3-methyl-4-((R)-1-((2R,3R,4R,5R,6R)-3,4,5-tris(benzyloxy)-6-((benzyloxy)methyl)tetrahydro-2H-pyran-2-yl)ethyl)phenyl)-5-(trifluoromethyl)pyridine (110 mg, 0.140 mmol) in DCM (5 mL) at −78° C., was added $BCl_3$ (1N in DCM, 1.117 mL, 1.117 mmol) under $N_2$. The reaction mixture was stirred at −78° C. for 1 h under $N_2$. The reaction mixture was quenched with MeOH (5 mL) and concentrated by rotary evaporator to get a residue. The residue was purified by Prep-HPLC with conditions: Column: XBridge Prep OBD C18 Column, 30×150 mm 5um; Mobile Phase A: Water (10 mmol/L $NH_4HCO_3$), Mobile Phase B: ACN; Flow rate:60 mL/min; Gradient:15 B to 38 B in 12 min; 254 nm; RT1:11.60; Injection Volume: 2.4 ml; Number of Runs:2; to afford the title product (25 mg, 0.058 mmol, 42% yield) as a white solid.

Formula: $C_{21}H_{24}F_3NO_5$ Exact Mass: 427.16 Molecular Weight: 427.42.

Analytical data: $^1$H NMR (400 MHz, Methanol-$d_4$) δ 9.08 (d, J=2.1 Hz, 1H), 8.91-8.78 (m, 1H), 8.34 (t, J=2.2 Hz, 1H), 7.61-7.47 (m, 3H), 4.22 (dd, J=10.2 Hz, 2.6 Hz, 1H), 4.10 (t, J=3.0 Hz, 1H), 3.82 (dd, J=8.6 Hz, 3.2 Hz, 1H), 3.72 (t, J=8.6 Hz, 1H), 3.60-3.52 (m, 2H), 3.42 (dd, J=11.6 Hz, 2.8 Hz, 1H), 3.24-3.20 (m, 1H), 2.51 (s, 3H), 1.28 (d, J=6.8 Hz, 3H). ESI-MS $[M+H]^+$ Calc'd for $(C_{21}H_{24}F_3NO_5H^+)$ 428.17, found, 428.05.

Example 5

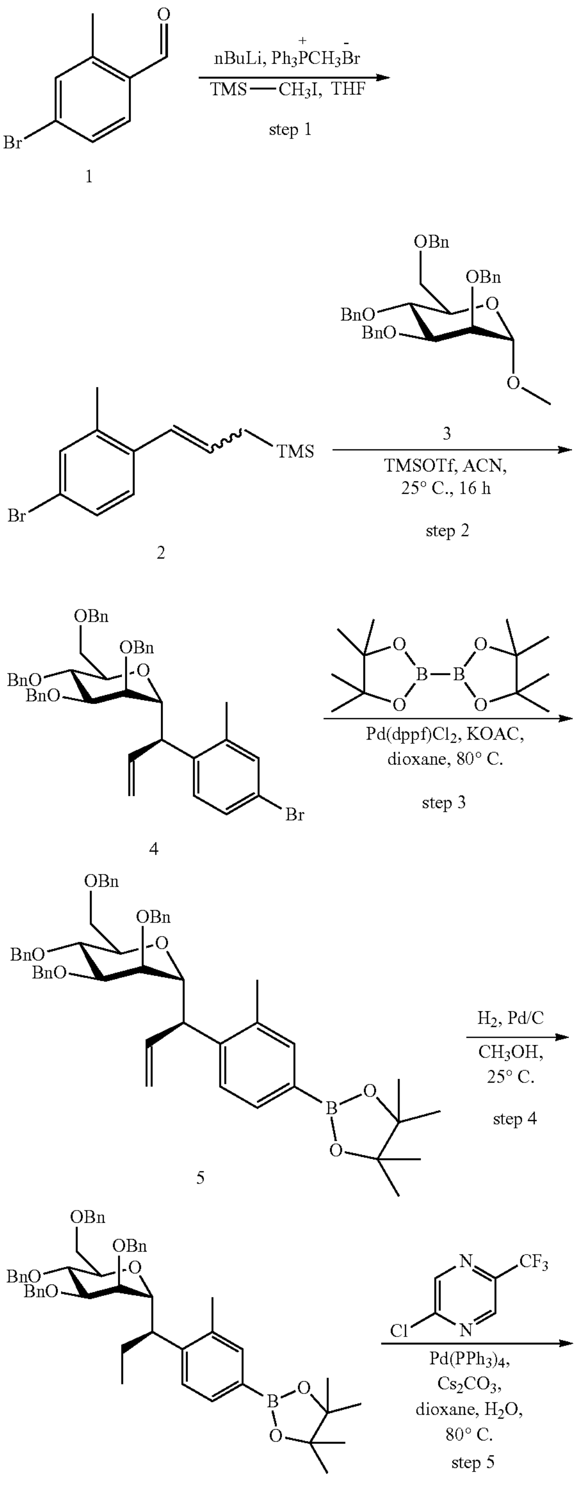

1

2

3

4

5

6

-continued

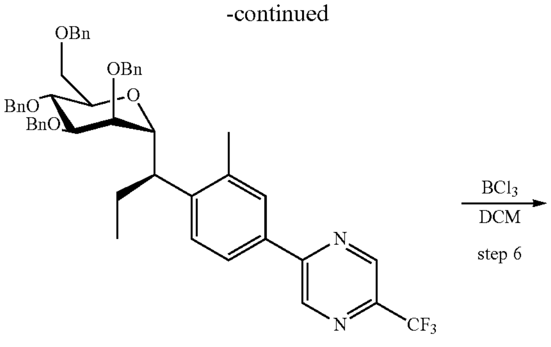

7

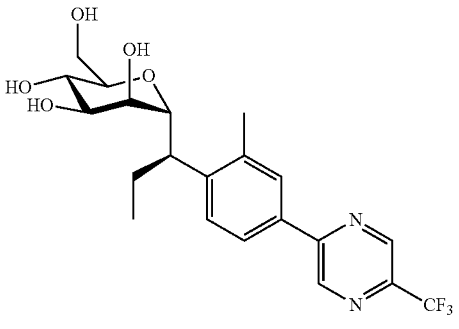

8

(2R,3S,4R,5S,6R)-2-(Hydroxymethyl)-6-((R)-1-(2-methyl-4-(5-(trifluoromethyl)pyrazin-2-yl)phenyl)propyl)tetrahydro-2H-pyran-3,4,5-triol

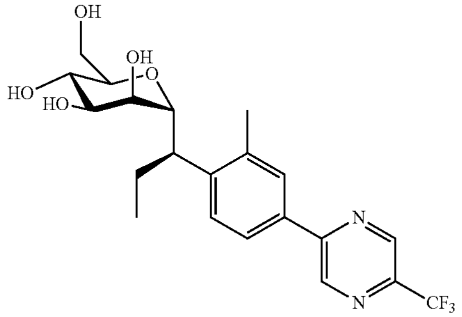

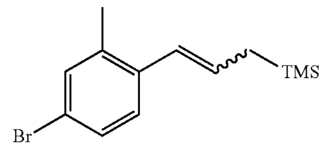

(3-(4-Bromo-2-methylphenyl)allyl)trimethylsilane

To a solution of $Ph_3PCH_3Br$ (65 g, 182 mmol) in THF (200 mL) was added nBuLi (80.5 mL, 201.3 mmol. 2.5 M in hexane) at 0° C. The resulting solution was warmed and stirred at 25° C. for 1 h. The solution was cooled to 0° C. and a solution of TMS-$CH_2$I (47 g, 219.5 mmol) in THE (200 mL) was added. The reaction mixture was stirred at 25° C. for 24 h. The reaction mixture was cooled to 0° C. and a solution of nBuLi (66.5 mL, 166.3 mmol, 2.5 M in hexane) was added. The reaction mixture was kept at 0° C. for 1 h, then cooled to −78° C. 4-Bromo-2-methylbenzaldehyde (30 g, 150.7 mmol) was added at −78° C., then reaction mixture was warmed to room temperature and stirred for 3 h. Upon completion, the reaction was quenched with aq. $NH_4Cl$ (200 mL). The organic layer was separated. The aqueous phase was extracted with ethyl acetate (150 mL×3). The combined organic layers were washed with brine (200 mL), dried over $Na_2SO_4$, and concentrated in vacuo. The residue was purified by column chromatography on silica gel using petroleum ether as eluent to afford title product (34.9 g, 81.8% yield, mixture of isomers) as a colorless oil. ESI-MS $[M+H]^+$ Calc'd for ($C_{13}H_{19}BrSiH^+$) 283.25, found, No Mass.

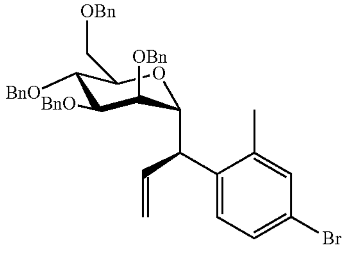

(2R,3R,4R,5R,6R)-3,4,5-Tris(benzyloxy)-2-((benzyloxy)methyl)-6-((R)-1-(4-bromo-2-methylphenyl)allyl)tetrahydro-2H-pyran To a solution of (2R,3R,4S,5S,6S)-3,4,5-tris(benzyloxy)-2-((benzyloxy)methyl)-6-methoxytetrahydro-2H-pyran (52 g, 93.7 mmol) in ACN (400 mL) was added (3-(4-bromo-2-methylphenyl) allyl)trimethylsilane (53 g, 187 mmol), and TMSOTf (31.2 g, 140.4 mmol) at 25° C. The resulting solution was stirred at 25° C. for 16 h. Upon completion, the reaction was quenched with water (150 mL). The organic layer was separated. The aqueous phase was extracted with ethyl acetate (100 mL×3). The combined organic layer washed with brine (100 mL), dried over $Na_2SO_4$, concentrated in vacuo. The residue was purified by column chromatography on silica gel using a gradient of 0-30% ethyl acetate in petroleum ether as eluent to afford a mixture (20 g) as a yellow oil. The mixture was further separated with Prep-SFC with conditions: Column: Phenomenex Lux Su Cellulose-3, 5*25 cm, 5 um; Mobile Phase A: $CO_2$: 50, Mobile Phase B: MeOH—Preparative: 50; Flow rate: 150 mL/min; 220 nm; Fraction at RT=10.32 min with MS signal of the desired product were collected and concentrated in vacuo to afford the title compound (5.5 g, 8% yield, minor isomer) as a yellow oil. ESI-MS $[M+NH_4]^+$ Calc'd for ($C_{44}H_{45}BrO_5$ $NH_4^+$) 750.28, found, 752.25. $^1$H NMR (300 MHz, Chloroform-d) δ 7.42-7.23 (m, 23H), 5.76-5.65 (m, 1H), 4.97 (d, J=12.0 Hz, 1H), 4.87-4.82 (m, 1H), 4.72-4.35 (m, 9H), 3.90-3.84 (m, 4H), 3.76-3.72 (m, 2H), 3.63-3.57 (m, 1H), 2.22 (s, 3H).

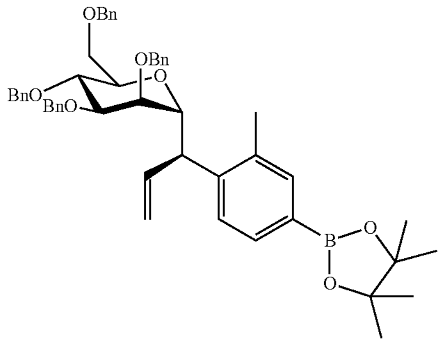

4,4,5,5-Tetramethyl-2-(3-methyl-4-((R)-1-((2R,3R,4R,5R,6R)-3,4,5-tris(benzyloxy)-6-((benzyloxy)methyl)tetrahydro-2H-pyran-2-yl)allyl)phenyl)-1,3,2-dioxaborolane To a solution of (2R,3R,4R,5R,6R)-3,4,5-Tris(benzyloxy)-2-((benzyloxy)methyl)-6-((R)-1-(4-bromo-2-methylphenyl)allyl)tetrahydro-2H-pyran (470 mg, 0.64 mmol) and 4,4,4',4',5,5,5',5'-octamethyl-2,2'-bi(1,3,2-dioxaborolane) (195 mg, 0.77 mmol) in 1,4-dioxane (10 mL) were added Pd(dppf)$Cl_2$·$CH_2Cl_2$, (52 mg, 0.064 mmol), KOAc (188 mg, 1.92 mmol) at 25° C. The reaction mixture was stirred at 80° C. for 16 h. After completion, the reaction mixture was concentrated to get a residue. The residue was dissolved with ethyl acetate, pre-adsorbed by evaporation on silica gel and loaded on the column, then purified by silica gel chromatography, eluting with EtOAc in petroleum (17%) to afford the title product (350 mg, 70% yield) as yellow oil. ESI-MS $[M+Na]^+$ Calc'd for ($C_{50}H_{57}BO_7Na^+$) 803.42, found, 803.42

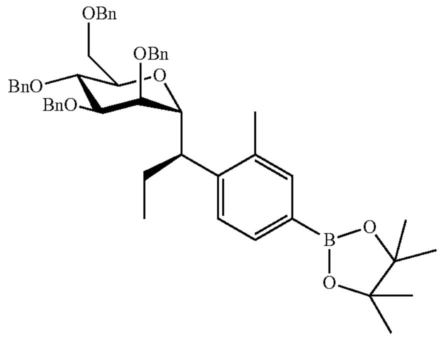

4,4,5,5-Tetramethyl-2-(3-methyl-4-((R)-1-((2R,3R,4R,5R,6R)-3,4,5-tris(benzyloxy)-6-((benzyloxy)methyl)tetrahydro-2H-pyran-2-yl)propyl)phenyl)-1,3,2-dioxaborolane To a solution of 4,4,5,5-tetramethyl-2-(3-methyl-4-((R)-1-((2R,3R,4R,5R,6R)-3,4,5-tris(benzyloxy)-6-((benzyloxy)methyl)tetrahydro-2H-pyran-2-yl)allyl)phenyl)-1,3,2-dioxaborolane (1.25 g, 1.6 mmol) in MeOH (30 mL) was added Pd/C (1.25 g) at 25° C. Then the reaction mixture was stirred at 25° C. for 3 h under $H_2$. After completion, the reaction mixture was filtered and filtrate was concentrated to give a residue. The residue was dissolved in DCM (10 mL), pre-adsorbed by evaporation onto silica gel and loaded to the column, then purified by silica gel chromatography, eluting with EtOAc in petroleum (17%) to afford the title product (800 mg, 64% yield) as a colorless oil, 79% pure. ESI-MS $[M+Na]^+$ Calc'd for ($C_{50}H_{59}BO_7$ $Na^+$) 805.44, found, 805.44.

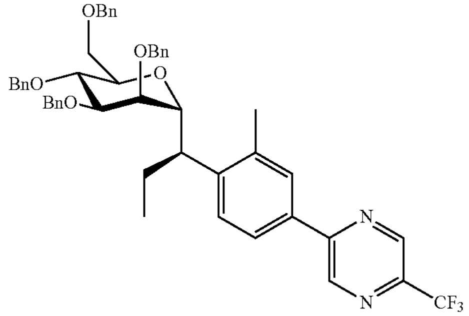

2-(3-Methyl-4-((R)-1-((2R,3R,4R,5R,6R)-3,4,5-tris(benzyloxy)-6-((benzyloxy)methyl)tetrahydro-2H-pyran-2-yl)propyl)phenyl)-5-(trifluoromethyl)pyrazine To a solution of 4,4,5,5-tetramethyl-2-(3-methyl-4-((R)-1-((2R,3R,4R,5R,6R)-3,4,5-tris(benzyloxy)-6-((benzyloxy)methyl)tetrahydro-2H-pyran-2-yl)propyl)phenyl)-1,3,2-dioxaborolane (200 mg, 0.26 mmol) in 1,4-dioxane (8 mL) and water (2 mL) was added 2-chloro-5-(trifluoromethyl)pyrazine (47 mg 0.26 mmol), $Pd(PPh_3)_4$ (30 mg 0.026 mmol) and $Cs_2CO_3$ (167 mg 0.51 mmol) at 25° C. Then, the reaction mixture was stirred for 1 h at 80° C. under $N_2$. After completion, the reaction was cooled to room temperature and the reaction mixture was quenched with water (10 mL) and extracted with ethyl acetate (3×10 mL) dried over $Na_2SO_4$ and filtered. The filtrate was concentrated under reduced pressure to give a residue. The residue was purified by silica gel chromatography, eluting with ethyl acetate in petroleum ether (19%) to afford the title product (150 mg, 72% yield) as a yellow oil. ESI-MS $[M+H]^+$ Calc'd for ($C_{49}H_{49}F_3N_2O_5H^+$) 803.36, found, 803.94.

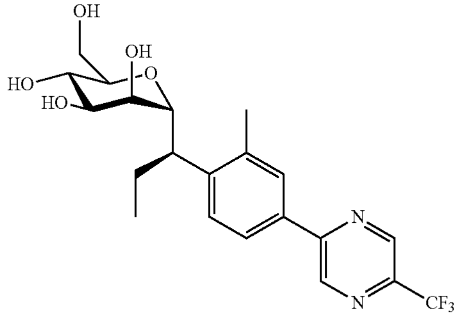

(2R,3S,4R,5S,6R)-2-(Hydroxymethyl)-6-((R)-1-(2-methyl-4-(5-(trifluoromethyl)pyrazin-2-yl)phenyl)propyl)tetrahydro-2H-pyran-3,4,5-triol To a solution of 2-(3-methyl-4-((R)-1-((2R,3R,4R,5R,6R)-3,4,5-tris(benzyloxy)-6-((benzyloxy)methyl)tetrahydro-2H-pyran-2-yl)propyl)phenyl)-5-(trifluoromethyl)

pyrazine (130 mg, 0.16 mmol) in DCM (5 mL) was added $BCl_3$ (1N in DCM, 1.3 mL, 1.3 mmol) at −78° C. under $N_2$. The reaction mixture was stirred at −78° C. for 1 h. The reaction mixture was quenched with MeOH (5 mL) and was concentrated to get a residue. The residue was purified by Prep-HPLC with conditions: Column: XBridge Prep C18 OBD Column 19×150 mm 5 um; Mobile Phase A: Water (10 mmol/L $NH_4HCO_3$), Mobile Phase B: ACN; Flow rate: 25 mL/min; Gradient: 30% B to 45% B in 8 min; 254 nm; Rt: 7.87 min to afford the desired product (40 mg, 57% yield) as a white solid.

Formula: $C_{21}H_{25}F_3N_2O_5$ Exact Mass: 442.17 Molecular Weight: 442.44.

Analytical data: $^1H$ NMR (400 MHz, Methanol-$d_4$) δ 9.28 (d, J=1.5 Hz, 1H), 9.13-8.99 (m, 1H), 8.03-8.01 (m, 2H), 7.59 (d, J=8.4 Hz, 1H), 4.19 (dd, J=8.8 Hz, 3.6 Hz, 1H), 3.99-3.98 (m, 1H), 3.84-3.69 (m, 2H), 3.63 (dd, J=11.7 Hz, 5.5 Hz, 1H), 3.50-3.35 (m, 2H), 3.28-3.24 (m, 1H), 2.53 (s, 3H), 1.93-1.86 (m, 1H), 1.73-1.65 (m, 1H), 0.83 (t, J=7.4 Hz, 3H). ESI-MS $[M+Na]^+$ Calc'd for $(C_{21}H_{25}F_3N_2O_5Na^+)$ 465.17, found, 465.

Example 6

(2R,3S,4R,5S,6R)-2-(Hydroxymethyl)-6-((R)-1-(2-methyl-4-(5-(trifluoromethyl)pyrazin-2-yl)phenyl)allyl)tetrahydro-2H-pyran-3,4,5-triol

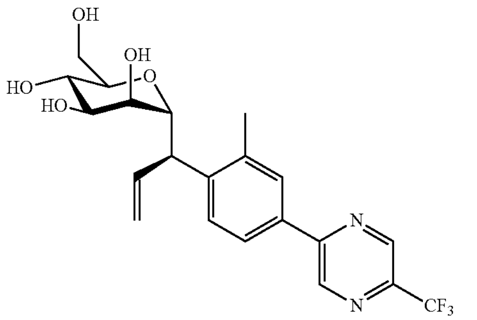

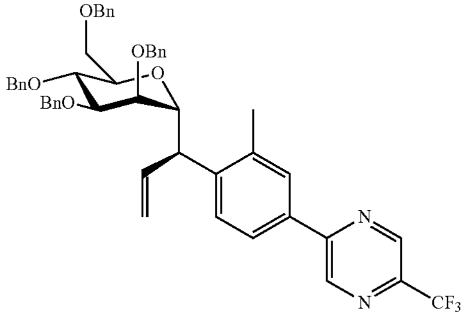

2-(3-Methyl-4-((R)-1-((2R,3R,4R,5R,6R)-3,4,5-tris(benzyloxy)-6-((benzyloxy)methyl)tetrahydro-2H-pyran-2-yl)allyl)phenyl)-5-(trifluoromethyl)pyrazine To a solution of 4,4,5,5-tetramethyl-2-(3-methyl-4-((R)-1-((2R,3R,4R,5R,6R)-3,4,5-tris(benzyloxy)-6-((benzyloxy)methyl)tetrahydro-2H-pyran-2-yl)allyl)phenyl)-1,3,2-dioxaborolane (250 mg, 0.32 mol) in 1,4-dioxane (8 mL) and water (2 mL) were added 2-chloro-5-(trifluoromethyl)pyrazine (59 mg 0.32 mmol), $Pd(PPh_3)_4$ (37 mg 0.032 mmol) and $Cs_2CO_3$ (209 mg 0.64 mmol) at 25° C. Then, the reaction mixture was stirred for 1 h at 80° C. under $N_2$. After completion, the reaction was cooled to 25° C. and the reaction mixture was quenched with water (10 mL) and extracted with ethyl acetate (3×10 mL), dried over $Na_2SO_4$ and filtered. The filtrate was concentrated under reduced pressure to give a residue. The residue was purified by silica gel chromatography, eluting with ethyl acetate in petroleum ether (14%) to afford the title product (250 mg, 97.5% yield) as yellow oil. ESI-MS $[M+Na]^+$ Calc'd for $(C_{49}H_{47}F_3N_2O_5Na^+)$ 823.33, found, 823.94.

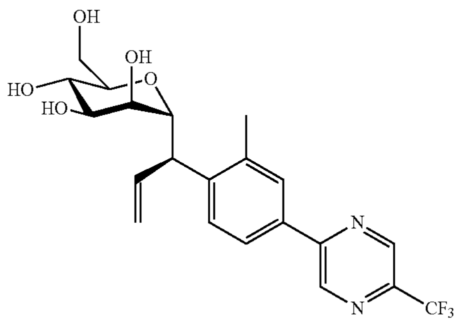

(2R,3S,4R,5S,6R)-2-(Hydroxymethyl)-6-((R)-1-(2-methyl-4-(5-(trifluoromethyl)pyrazin-2-yl)phenyl)allyl)tetrahydro-2H-pyran-3,4,5-triol To a solution of 2-(3-methyl-4-((R)-1-((2R,3R,4R,5R,6R)-3,4,5-tris(benzyloxy)-6-((benzyloxy)methyl)tetrahydro-2H-pyran-2-yl)allyl)phenyl)-5-(trifluoromethyl)pyrazine (230 mg, 0.29 mmol) in DCM (5 mL) was added $BCl_3$ (1N in DCM, 2.3 mL, 2.3 mmol) at −78° C. under $N_2$. The reaction mixture was stirred at −78° C. for 1 h. The reaction mixture was quenched with MeOH (5 mL) and concentrated in vacuo to get a residue. The residue was purified by Prep-HPLC with conditions: Column: XBridge Shield RP18 OBD Column 30*150 mm, 5 um; Mobile Phase A: Water (10 mmol/L $NH_4HCO_3$+0.1% $NH_3 \cdot H_2O$), Mobile Phase B: ACN; Flow rate: 60 mL/min; Gradient: 25% B to 51% B in 9 min; 220 nm; Rt: 7.47 min to afford the title product (82 mg, 64% yield) as a white solid.

Formula: $C_{21}H_{23}F_3N_2O_5$ Exact Mass: 440.16 Molecular Weight: 440.42.

Analytical data: $^1H$ NMR (300 MHz, Methanol-d4) δ 9.28 (d, J=1.4 Hz, 1H), 9.04 (d, J=1.4 Hz, 1H), 8.06-8.03 (m, 2H), 7.64-7.54 (m, 1H), 5.98-5.87 (m, 1H), 5.30-5.09 (m, 2H), 4.42 (dd, J=10.8 Hz, 2.0 Hz, 1H), 4.25-4.07 (m, 2H), 3.89 (dd, J=9.0 Hz, 3.3 Hz, 1H), 3.74 (t, J=9.1 Hz, 1H), 3.57 (dd, J=11.7 Hz, 4.8 Hz, 1H), 3.41 (dd, J=11.7 Hz, 2.8 Hz, 1H), 3.23-3.18 (m, 1H), 2.52 (s, 3H). ESI-MS $[M+H]^+$ Calc'd for $(C_{21}H_{23}F_3N_2O_5H^+)$ 441.16, found, 441.20.

Example 7

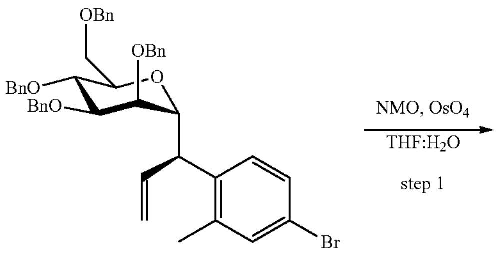

-continued

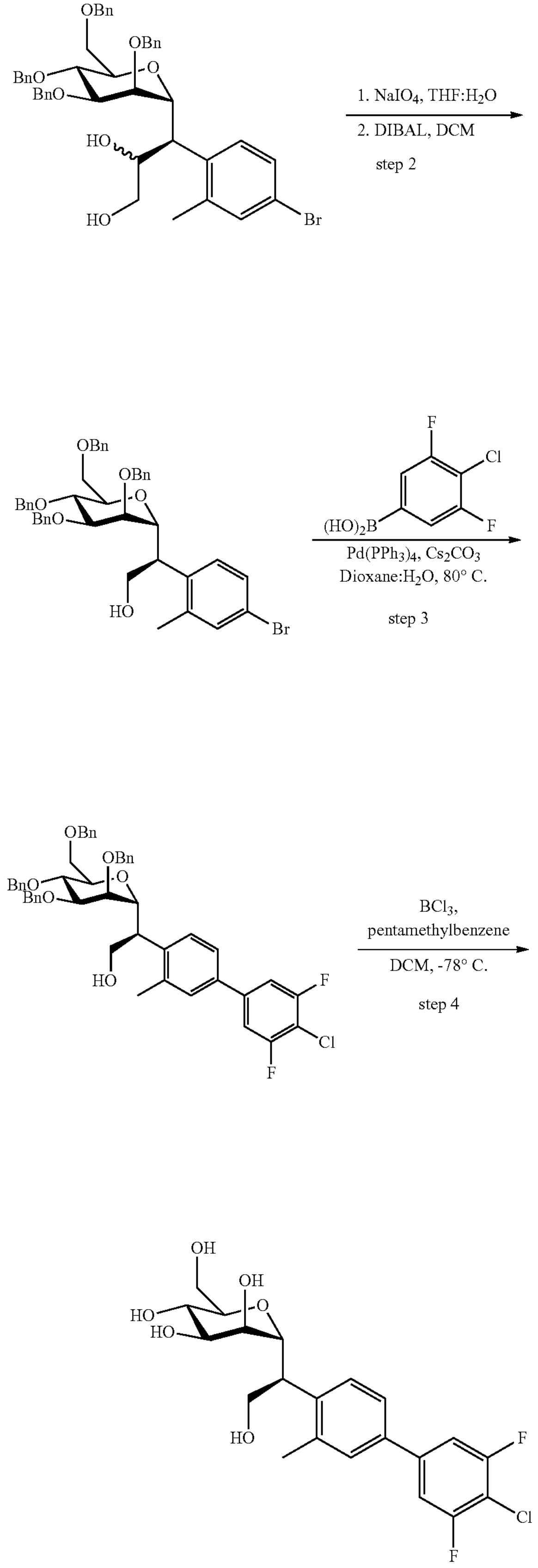

(2R,3S,4R,5S,6R)-2-((S)-1-(4'-chloro-3',5'-difluoro-3-methyl-[1,1'-biphenyl]-4-yl)-2-hydroxyethyl)-6-(hydroxymethyl)tetrahydro-2H-pyran-3,4,5-triol

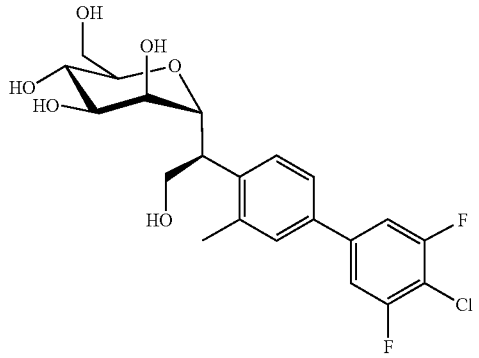

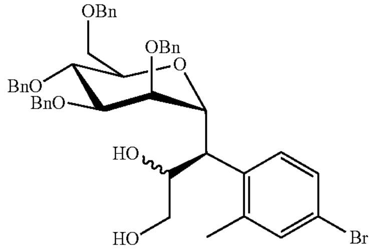

(S)-3-(4-bromo-2-methylphenyl)-3-((2R,3R,4R,5R,6R)-3,4,5-tris(benzyloxy)-6-((benzyloxy)methyl)tetrahydro-2H-pyran-2-yl)propane-1,2-diol To a solution of (2R,3R,4R,5R,6R)-3,4,5-Tris(benzyloxy)-2-((benzyloxy)methyl)-6-((R)-1-(4-bromo-2-methylphenyl)allyl)tetrahydro-2H-pyran (600 mg, 0.82 mmol) in THE (10 mL) and water (5 mL) was added N-methylmorpholine-N-oxide (384 mg, 3.28 mmol) under $N_2$. Osmium tetroxide (2.5% wt. in t-BuOH; 2.92 g, 0.29 mmol) was added dropwise, and the reaction was stirred 24 h at 25° C. Upon completion, saturated $Na_2S_2O_3$(aq) was added and the reaction mixture was stirred until a black precipitate formed. The reaction mixture was then extracted with ethyl acetate (30 mL×4). The combined organic layers were washed with brine (200 mL), dried over $Na_2SO_4$, and concentrated in vacuo. The residue was purified by column chromatography on silica gel using a gradient of 0~50% ethyl acetate in hexanes as eluent, wherein the two separable isomers were collected together to afford the title product (557.3 mg, 88.5% yield, mixture of isomers) as a colorless syrup. ESI-MS $[M+NH]^+$ Calc'd for $(C_{44}H_{47}BrO_7H^+)$ 789.24, found, 789.2.

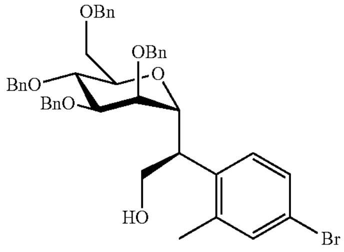

(S)-2-(4-bromo-2-methylphenyl)-2-((2R,3R,4R,5R,6R)-3,4,5-tris(benzyloxy)-6-((benzyloxy)methyl)tetrahydro-2H-pyran-2-yl)ethan-1-ol To a solution of(S)-3-(4-bromo-2-methylphenyl)-3-((2R,3R,4R,5R,6R)-3,4,5-tris(benzyloxy)-6-((benzyloxy)methyl)tetrahydro-2H-pyran-2-yl)propane-1,2-diol (125 mg, 0.16 mmol) in THE (1.5 mL) and water (0.6 mL) was added $NaIO_4$ (87 mg, 0.41 mmol). The reaction mixture was stirred for 2 h at 25° C. Upon completion, the reaction was quenched with ice water (5 mL), extracted with DCM (5 mL×3), the organic phases were combined, washed with brine (20 mL), dried over $Na_2SO_4$ and concentrated in vacuo (without heating) to get the aldehyde intermediate as a syrup. ESI-MS $[M+Na]^+$ Calc'd for ($C_{43}H_{44}BrO_6$ $Na^+$) 758.22, found, 759.1. Once dry, the crude aldehyde was dissolved in DCM (1 mL) under $N_2$ and cooled to 0° C. DIBAL (1M in hexanes; 0.24 mL, 0.24 mmol) was added dropwise and the reaction mixture was stirred for 30 min at 0° C., then allowed to warm to room temperature overnight. Upon completion, the reaction mixture was diluted with DCM (5 mL) and was carefully quenched with the addition of ice. The reaction mixture was washed with [1N] HCl (aq) (5 mL×3) followed by brine (5 mL×1), then dried over $Na_2SO_4$, and concentrated in vacuo. The residue was purified by column chromatography on silica gel using a gradient of 0~50% ethyl acetate in hexanes as eluent to afford the title product (68.3 mg, 56.8% yield). ESI-MS $[M+Na]^+$ Calc'd for ($C_{43}H_{45}BrO_6Na^+$) 759.23, found, 759.1.

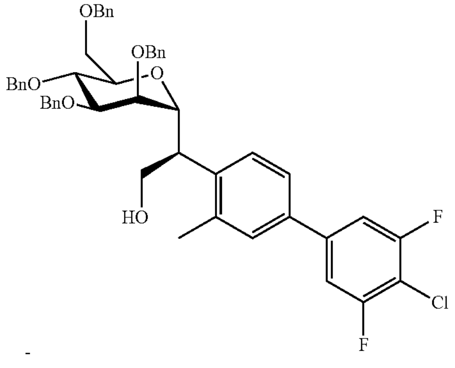

(S)-2-(4'-chloro-3',5'-difluoro-3-methyl-[1,1'-biphenyl]-4-yl)-2-((2R,3R,4R,5R,6R)-3,4,5-tris(benzyloxy)-6-((benzyloxy)methyl)tetrahydro-2H-pyran-2-yl)ethan-1-ol To a flask under $N_2$ was added a solution of (S)-2-(4-bromo-2-methylphenyl)-2-((2R,3R,4R,5R,6R)-3,4,5-tris(benzyloxy)-6-((benzyloxy)methyl)tetrahydro-2H-pyran-2-yl)ethan-1-ol (68 mg, 0.093 mol) in 1,4-dioxane (5 mL) and water (1 mL), followed by the sequential addition of (4-chloro-3,5-difluorophenyl)boronic acid (35.6 mg 0.19 mmol), $Cs_2CO_3$ (75.4 mg 0.23 mmol) and $Pd(PPh_3)_4$ (16.0 mg 0.013 mmol). The reaction was purged with $N_2$ three times, and then placed into an oil bath at 80° C. The reaction mixture was stirred for 2 h at 80° C. After completion, the reaction was cooled to room temperature and concentrated under reduced pressure to give a residue. The residue was partially purified by column chromatography on silica gel using a gradient of 0-50% ethyl acetate in hexanes as eluent to afford the title product (72.1 mg, 96.2% yield) as a yellow syrup. ESI-MS $[M+Na]^+$ Calc'd for ($C_{49}H_{47}ClF_{206}Na^+$) 827.29, found, 827.3.

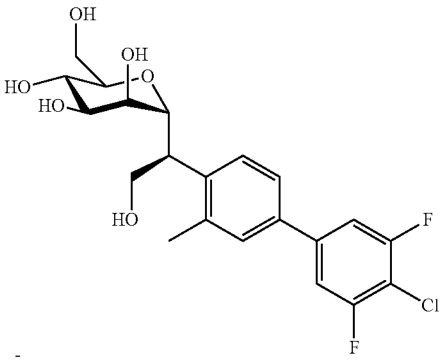

(2R,3S,4R,5S,6R)-2-((S)-1-(4'-chloro-3',5'-difluoro-3-methyl-[1,1'-biphenyl]-4-yl)-2-hydroxyethyl)-6-(hydroxymethyl)tetrahydro-2H-pyran-3,4,5-triol To a solution of (S)-2-(4'-chloro-3',5'-difluoro-3-methyl-[1,1'-biphenyl]-4-yl)-2-((2R,3R,4R,5R,6R)-3,4,5-tris(benzyloxy)-6-((benzyloxy)methyl)tetrahydro-2H-pyran-2-yl)ethan-1-ol (72.1 mg, 0.90 mmol) and pentamethylbenzene (199 mg, 1.34 mmol) in DCM (1 mL) was dropwise added $BCl_3$ (1N in DCM, 1.34 mL, 1.34 mmol) at −78° C. The resulting solution was stirred for 1 h at −78° C. Upon completion, the reaction was quenched with MeOH (0.5 mL), brought to room temperature and concentrated under reduced pressure to get a residue. The residue was purified by Prep-HPLC with conditions: Column: Teledyne Isco RediSep Prep C18 Column, 20×150 mm, 5 um; Mobile Phase A: Water (0.05% TFA), Mobile Phase B: ACN (0.05% TFA); Flow rate: 18.9 mL/min; Gradient: 10% B to 39% B in 35 min; 254/214 nm; Rt: 33 min) to give the title compound (16.3 mg, 51.2%) as a white solid.

Formula: $C_{21}H_{23}ClF_2O_6$ Exact Mass: 444.12 Molecular Weight: 444.86.

Analytical data: $^1H$ NMR (400 MHz, Methanol-$d_4$) δ 7.60 (d, J=8.2 Hz, 1H), 7.47-7.36 (m, 4H), 4.34 (t, J=6.7 Hz, 1H), 3.95-3.78 (m, 4H), 3.74-3.63 (m, 2H), 3.62-3.54 (m, 1H), 3.47-3.40 (m, 2H), 2.48 (s, 3H). ESI-MS $[M+H]^+$ Calc'd for ($C_{21}H_{23}ClF_2O_6Na^+$) 467.10, found, 467.0.

Table 1 provides compounds prepared and their biological and pharmacokinetic data (in rat), if tested.

TABLE 1

| Structure | Example # And/or Compound # | HAI | DNAUC oral h*uM | %F | Ue% po | LCMS |
|---|---|---|---|---|---|---|
| 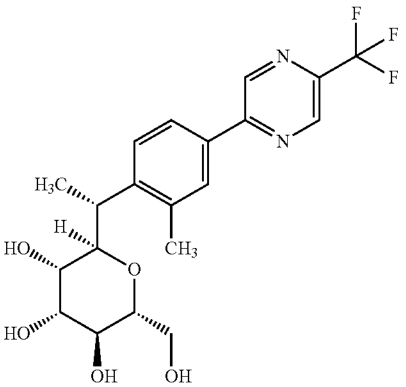 [SMILES: Cc1cc(-c2cnc(C(F)(F)F)cn2)ccc1[C@@H](C)[C@H]1O[C@H](CO)[C@@H](O)[C@H](O)[C@@H]1O] | 1 | "++++" | "++" | "+++" | "+++" | ESI-MS $[M + Na]^+$ Calc'd for $(C_{20}H_{23}F_3N_2O_5Na^+)$, 451.15, found, 451.10. |
| 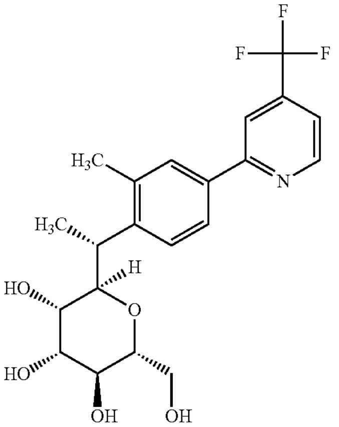 [SMILES: Cc1cc(-c2cc(C(F)(F)F)ccn2)ccc1[C@@H](C)[C@H]1O[C@H](CO)[C@@H](O)[C@H](O)[C@@H]1O] | 2 | "+++" | "++" | "+++" | "++" | ESI-MS $[M + H]^+$ Calc'd for $(C_{21}H_{24}F_3NO_5Na^+)$ 428.17, found, 450.10. |
| 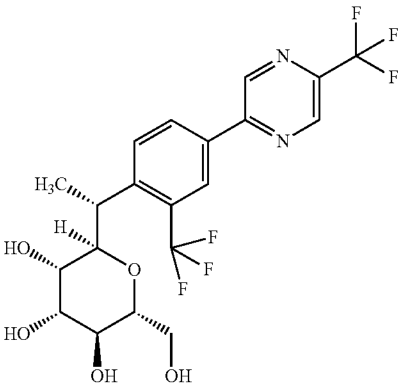 [SMILES: C[C@H](c1ccc(-c2cnc(C(F)(F)F)cn2)cc1C(F)(F)F)[C@H]1O[C@H](CO)[C@@H](O)[C@H](O)[C@@H]1O] | 3 | "++++" | "+++" | "+++" | "+++" | ESI-MS $[M + H]^+$ Calc'd for $(C_{20}H_{20}F_6N_2O_5H^+)$ 483.14, found, 483.05. |

TABLE 1-continued
| Structure | Example # And/or Compound # | HAI | DNAUC oral h*uM | %F | Ue% po | LCMS |
|---|---|---|---|---|---|---|
| 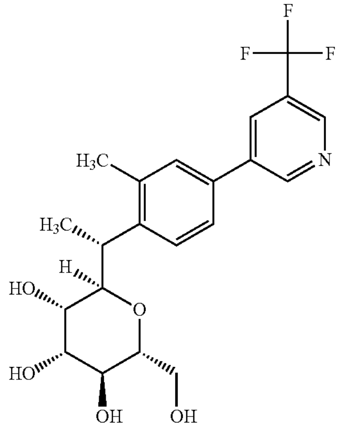 [SMILES: Cc1cc(-c2cncc(C(F)(F)F)c2)ccc1[C@@H](C)[C@H]1O[C@H](CO)[C@@H](O)[C@H](O)[C@@H]1O] | 4 | "++++" | "++" | "+++" | "+++" | ESI-MS $[M + H]^+$ Calc'd for ($C_{21}H_{24}F_3NO_5H^+$) 428.17, found, 428.05. |
| 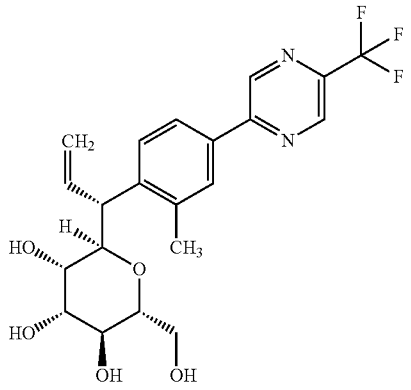 [SMILES: C=C[C@H](c1ccc(-c2cnc(C(F)(F)F)cn2)cc1C)[C@H]1O[C@H](CO)[C@@H](O)[C@H](O)[C@@H]1O] | 5 | "+++" | "+" | "++" | "++" | ESI-MS $[M + H]^+$ Calc'd for ($C_{21}H_{23}F_3N_2O_5H^+$) 441.16, found, 441.20. |
| 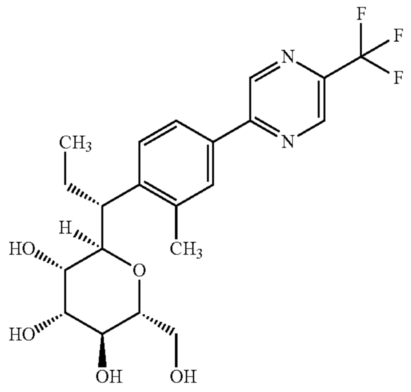 [SMILES: CC[C@H](c1ccc(-c2cnc(C(F)(F)F)cn2)cc1C)[C@H]1O[C@H](CO)[C@@H](O)[C@H](O)[C@@H]1O] | 6 | "+++" | "+" | "++" | | ESI-MS [M + Na]+ Calc'd for ($C_{21}H_{25}F_3N_2O_5Na+$) 465.17, found, 465. |

TABLE 1-continued
| Structure | Example # And/or Compound # | HAI | DNAUC oral h*uM | %F | Ue% po | LCMS |
|---|---|---|---|---|---|---|
| 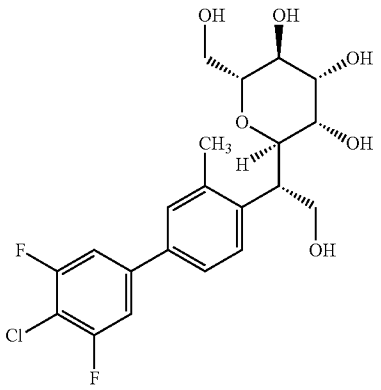 [SMILES: Cc1cc(-c2cc(F)c(Cl)c(F)c2)ccc1[C@@H](CO)[C@H]1O[C@H](CO)[C@@H](O)[C@H](O)[C@@H]1O] | 7 | "++++" | "++" | "++" | "++" | ESI-MS [M − H]$^-$ Calc'd for ($C_{21}H_{23}ClF_2O_6$-$H^+$) 443.12, found, 443.12. |
| 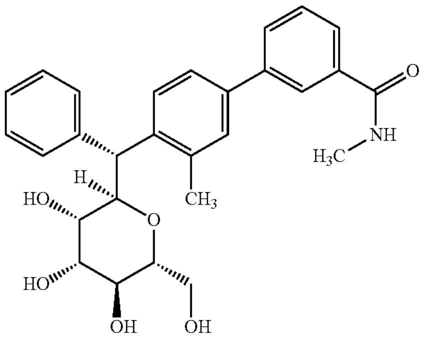 [SMILES: CNC(=O)c1cccc(-c2ccc([C@@H](c3ccccc3)[C@H]3O[C@H](CO)[C@@H](O)[C@H](O)[C@@H]3O)c(C)c2)c1] | 8 | "+++" | | | | ESI-MS [M + H]$^+$ Calc'd for ($C_{28}H_{31}O_6H^+$) 478.2, found, 478.05. |
| 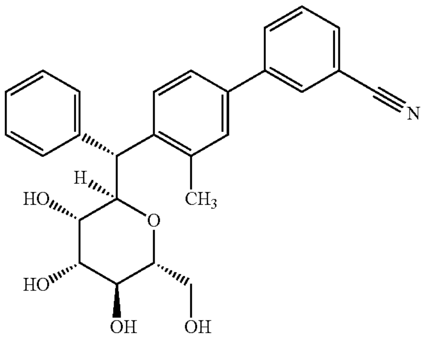 [SMILES: Cc1cc(-c2cccc(C#N)c2)ccc1[C@@H](c1ccccc1)[C@H]1O[C@H](CO)[C@@H](O)[C@H](O)[C@@H]1O] | 9 | "++" | | | | ESI-MS [M + Na]+ Calc'd for ($C_{27}H_{27}N_2O_5Na$+) 468.2, found, 468.18. |
| 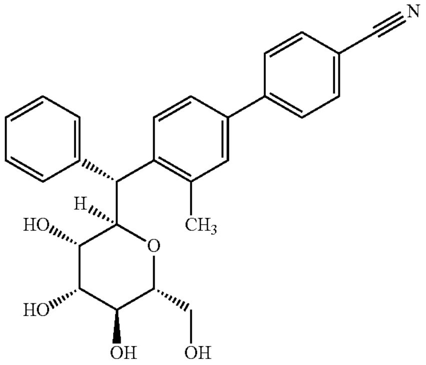 [SMILES: Cc1cc(-c2ccc(C#N)cc2)ccc1[C@@H](c1ccccc1)[C@H]1O[C@H](CO)[C@@H](O)[C@H](O)[C@@H]1O] | 10 | "+++" | | | | ESI-MS [M + Na]+ Calc'd for ($C_{27}H_{27}N_2O_5Na$+) 468.2, found, 468.18. |

TABLE 1-continued
| Structure | Example # And/or Compound # | HAI | DNAUC oral h*uM | %F | Ue% po | LCMS |
|---|---|---|---|---|---|---|
| 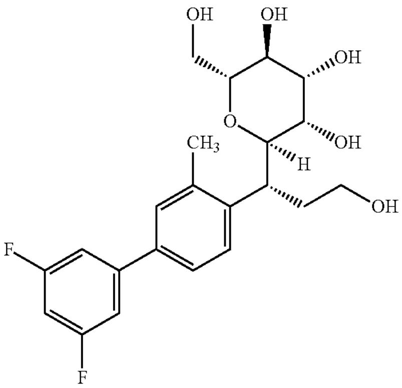 [SMILES: Cc1cc(-c2cc(F)cc(F)c2)ccc1[C@@H](CCO)[C@H]1O[C@H](CO)[C@@H](O)[C@H](O)[C@@H]1O] | 11 | "+++" | | | | ESI-MS [M + H]$^+$ Calc'd for ($C_{22}H_{26}F_2O_6H^+$) 425.17, found, 425.17. |
| 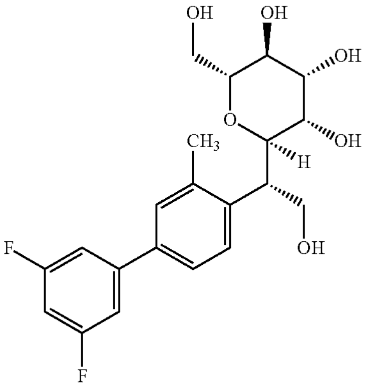 [SMILES: Cc1cc(-c2cc(F)cc(F)c2)ccc1[C@@H](CO)[C@H]1O[C@H](CO)[C@@H](O)[C@H](O)[C@@H]1O] | 12 | "+++" | | | | ESI-MS [M + H]$^+$ Calc'd for ($C_{21}H_{24}F_2O_6H^+$) 411.15, found, 411.15. |
| 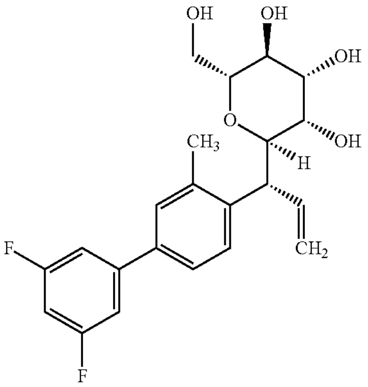 [SMILES: C=C[C@H](c1ccc(-c2cc(F)cc(F)c2)cc1C)[C@H]1O[C@H](CO)[C@@H](O)[C@H](O)[C@@H]1O] | 13 | "++" | | | | ESI-MS [M + H]$^+$ Calc'd for ($C_{22}H_{24}F_2O_5H^+$) 407.16, found, 407.16. |
| 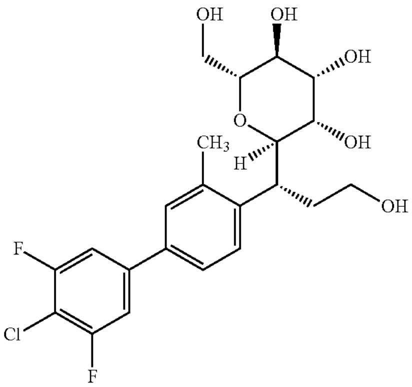 [SMILES: Cc1cc(-c2cc(F)c(Cl)c(F)c2)ccc1[C@@H](CCO)[C@H]1O[C@H](CO)[C@@H](O)[C@H](O)[C@@H]1O] | 14 | "++++" | "+" | | | ESI-MS [M + H]$^+$ Calc'd for ($C_{22}H_{25}ClF_2O_6H^+$) 459.13, found, 459.13. |

TABLE 1-continued
| Structure | Example # And/or Compound # | HAI | DNAUC oral h*uM | %F | Ue% po | LCMS |
|---|---|---|---|---|---|---|
| 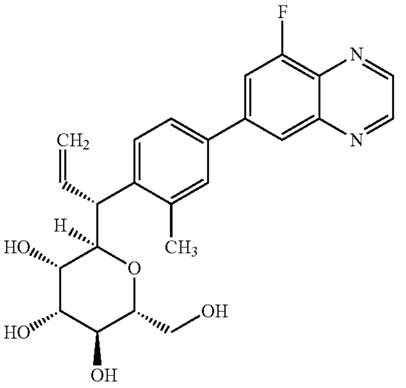 [SMILES: C=C[C@H](c1ccc(-c2cc(F)c3nccnc3c2)cc1C)[C@H]1O[C@H](CO)[C@@H](O)[C@H](O)[C@@H]1O] | 15 | "++++" | "+" | | | ESI-MS $[M + H]^+$ Calc'd for $(C_{24}H_{25}FN_2O_5H^+)$ 441.2, found, 441.18. |
| 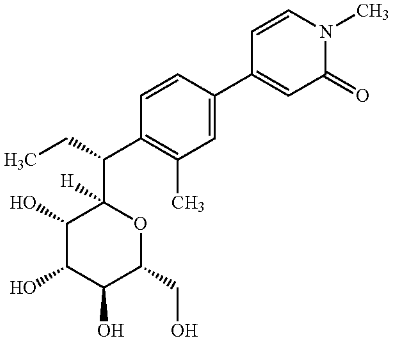 [SMILES: CC[C@H](c1ccc(-c2ccn(C)c(=O)c2)cc1C)[C@H]1O[C@H](CO)[C@@H](O)[C@H](O)[C@@H]1O] | 16 | "+++" | "+" | | | ESI-MS $[M + H]^+$ Calc'd for $(C_{22}H_{29}NO_6H^+)$ 404.47, found, 404.21. |
| 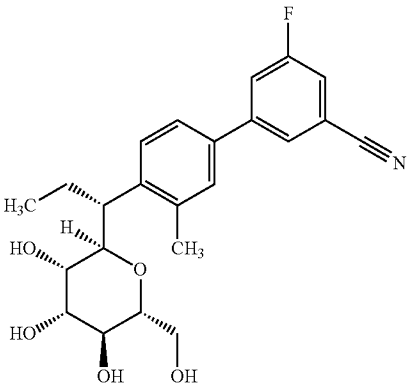 [SMILES: CC[C@H](c1ccc(-c2cc(F)cc(C#N)c2)cc1C)[C@H]1O[C@H](CO)[C@@H](O)[C@H](O)[C@@H]1O] | 17 | "+++" | "+" | | | ESI-MS $[M + NH_4]^+$ Calc'd for $(C_{23}H_{26}FNO_5NH_4^+)$ 433.2, found, 433.21. |
| 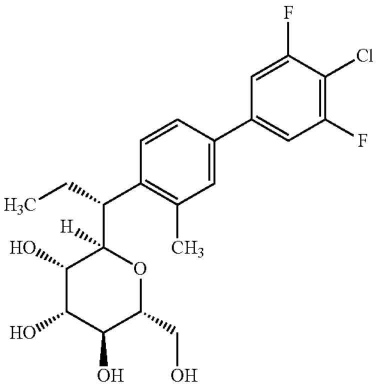 [SMILES: CC[C@H](c1ccc(-c2cc(F)c(Cl)c(F)c2)cc1C)[C@H]1O[C@H](CO)[C@@H](O)[C@H](O)[C@@H]1O] | 18 | "++" | | | | ESI-MS $[M + NH_4]^+$ Calc'd for $(C_{23}H_{26}Cl_2F_2O_5NH_4^+)$ 460.14, found, 460.17. |

TABLE 1-continued
| Structure | Example # And/or Compound # | HAI | DNAUC oral h*uM | %F | Ue% po | LCMS |
|---|---|---|---|---|---|---|
| 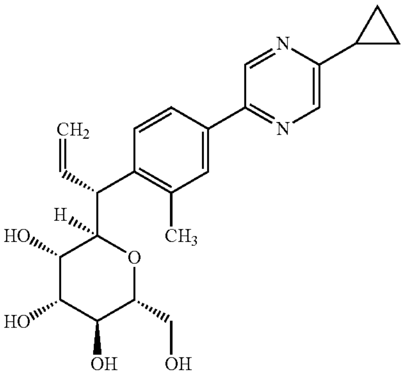 [SMILES: C=C[C@H](c1ccc(-c2cnc(C3CC3)cn2)cc1C)[C@H]1O[C@H](CO)[C@@H](O)[C@H](O)[C@@H]1O] | 19 | "++++" | "+" | | | ESI-MS [M + Na]+ Calc'd for ($C_{23}H_{28}N_2O_5Na+$) 435.49, found, 435.2. |
| 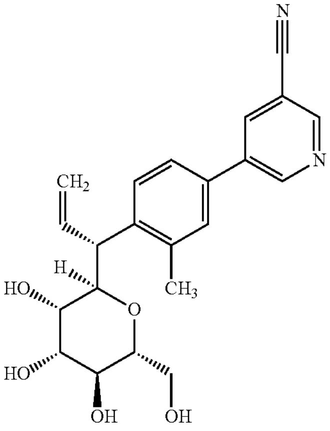 [SMILES: C=C[C@H](c1ccc(-c2cncc(C#N)c2)cc1C)[C@H]1O[C@H](CO)[C@@H](O)[C@H](O)[C@@H]1O] | 20 | "+++" | | | | ESI-MS $[M + Na]^+$ Calc'd for ($C_{22}H_{24}N_2O_5Na^+$) 419.2, found, 419.15. |
| 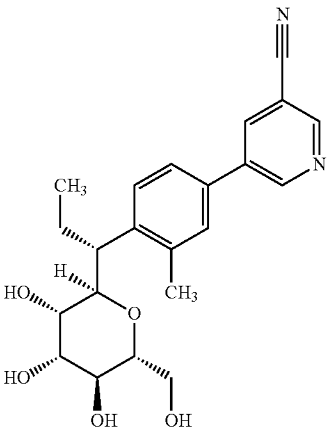 [SMILES: CC[C@H](c1ccc(-c2cncc(C#N)c2)cc1C)[C@H]1O[C@H](CO)[C@@H](O)[C@H](O)[C@@H]1O] | 21 | "+++" | "+" | | | ESI-MS $[M + H]^+$ Calc'd for ($C_{22}H_{26}N_2O_5H^+$) 399.2, found, 399.19. |

TABLE 1-continued
| Structure | Example # And/or Compound # | HAI | DNAUC oral h*uM | %F | Ue% po | LCMS |
|---|---|---|---|---|---|---|
| 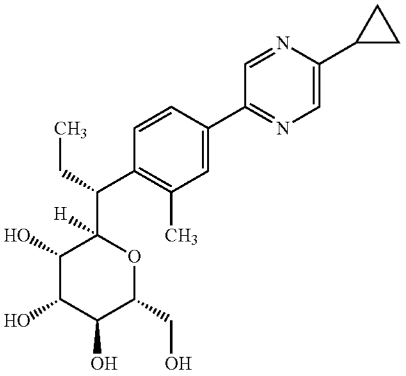 [SMILES: CC[C@H](c1ccc(-c2cnc(C3CC3)cn2)cc1C)[C@H]1O[C@H](CO)[C@@H](O)[C@H](O)[C@@H]1O] | 22 | "+++" | | | | ESI-MS $[M + Na]^+$ Calc'd for $(C_{23}H_{30}N_2O_5Na^+)$ 437.49, found, 437.22. |
| 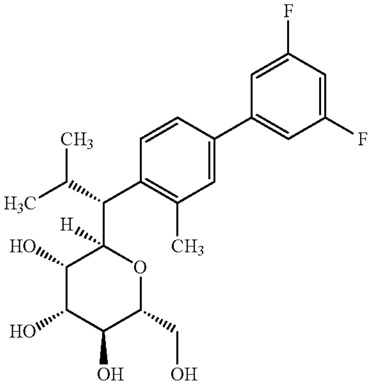 [SMILES: Cc1cc(-c2cc(F)cc(F)c2)ccc1[C@@H](C(C)C)[C@H]1O[C@H](CO)[C@@H](O)[C@H](O)[C@@H]1O] | 23 | "+" | | | | ESI-MS $[M + NH_4]^+$ Calc'd for $(C_{23}H_{28}F_2O_5NH_4^+)$ 440.22, found, 440.30. |
| 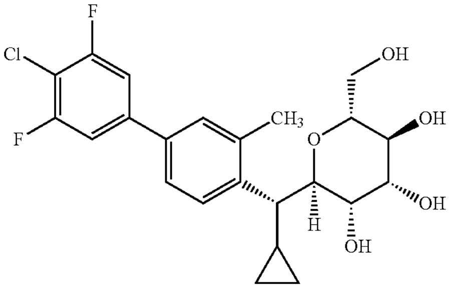 [SMILES: Cc1cc(-c2cc(F)c(Cl)c(F)c2)ccc1[C@@H](C1CC1)[C@H]1O[C@H](CO)[C@@H](O)[C@H](O)[C@@H]1O] | 25 | "+++" | | | | ESI-MS $[M + H]^+$ Calc'd for $(C_{23}H_{29}ClF_2O_5H^+)$, 455.1, found, 455.136. |
| 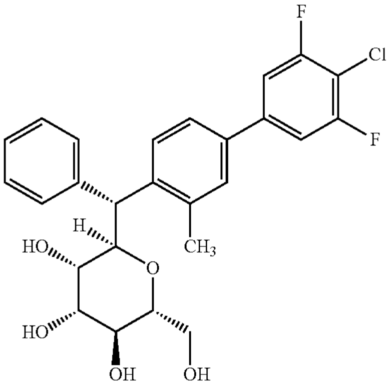 [SMILES: Cc1cc(-c2cc(F)c(Cl)c(F)c2)ccc1[C@@H](c1ccccc1)[C@H]1O[C@H](CO)[C@@H](O)[C@H](O)[C@@H]1O] | 26 | "+++" | | | | ESI-MS [M + NH4]+ Calc'd for (C26H25ClF2O5NH4+) 508.14, found, 508.20. |

TABLE 1-continued
| Structure | Example # And/or Compound # | HAI | DNAUC oral h*uM | %F | Ue% po | LCMS |
|---|---|---|---|---|---|---|
| 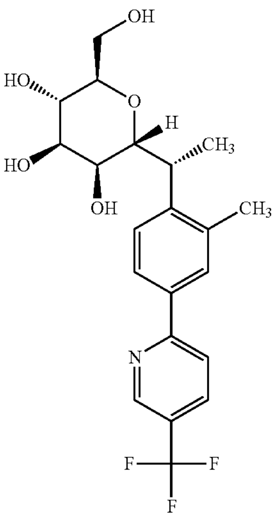 [SMILES: Cc1cc(-c2ccc(C(F)(F)F)cn2)ccc1[C@@H](C)[C@H]1O[C@H](CO)[C@@H](O)[C@H](O)[C@@H]1O] | 27 | "+++" | | | | ESI-MS $[M + H]^+$ Calc'd for $(C_{21}H_{24}F_3NO_5H^+)$ 428.17, found, 428.10. |
| 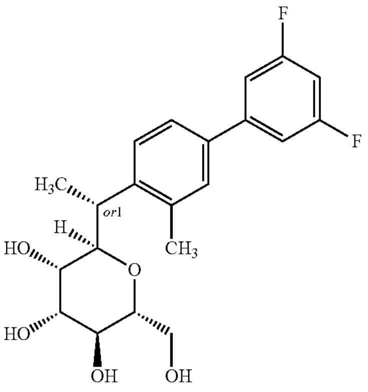 ISOMER 1 | 28 | "+++" | | | | ESI-MS $[M + Na]^+$ Calc'd for $(C_{21}H_{24}F_2O_5\ Na^+)$, 417.15, found, 412.25. |
| 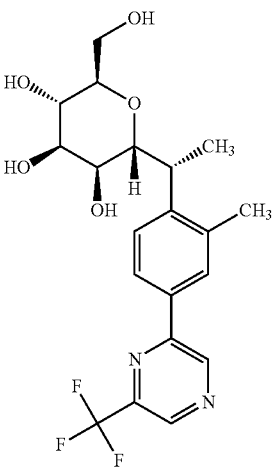 [SMILES: Cc1cc(-c2cncc(C(F)(F)F)n2)ccc1[C@@H](C)[C@H]1O[C@H](CO)[C@@H](O)[C@H](O)[C@@H]1O] | 29 | "++++" | "+" | "++" | "++" | ESI-MS $[M + H]^+$ Calc'd for $(C_{20}H_{23}F_3N_2O_5Na^+)$, 429.2, found, 429.2. |

TABLE 1-continued
| Structure | Example # And/or Compound # | HAI | DNAUC oral h*uM | %F | Ue% po | LCMS |
|---|---|---|---|---|---|---|
| 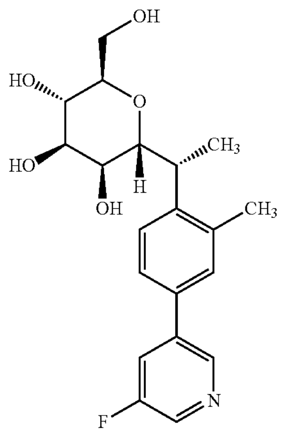 [SMILES: Cc1cc(-c2cncc(F)c2)ccc1[C@@H](C)[C@H]1O[C@H](CO)[C@@H](O)[C@H](O)[C@@H]1O] | 30 | "+++" | | | | ESI-MS $[M + H]^+$ Calc'd for $(C_{20}H_{24}FNO_5H^+)$ 378.4, found, 378.2. |
| 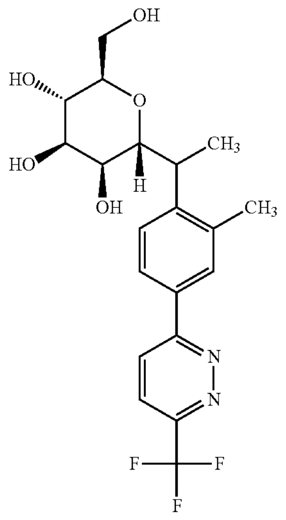 [SMILES: Cc1cc(-c2ccc(C(F)(F)F)nn2)ccc1C(C)[C@H]1O[C@H](CO)[C@@H](O)[C@H](O)[C@@H]1O] | 31 | "++++" | | | | ESI-MS $[M + Na]^+$ Calc'd for $(C_{20}H_{23}F_3N2O_5Na^+)$ 451.17, found, 451.05. |
| 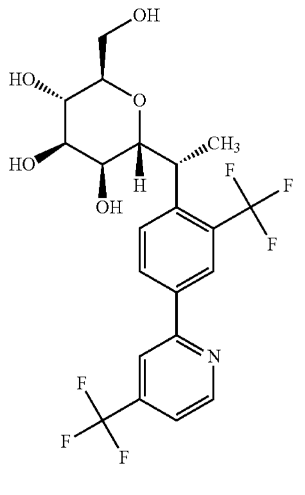 [SMILES: C[C@H](c1ccc(-c2cc(C(F)(F)F)ccn2)cc1C(F)(F)F)[C@H]1O[C@H](CO)[C@@H](O)[C@H](O)[C@@H]1O] | 32 | "+++" | | | | ESI-MS $[M + H]^+$ Calc'd for $(C_{21}H_{21}F_6NO_5H^+)$ 482.14, found, 482.14 |

TABLE 1-continued

| Structure | Example # And/or Compound # | HAI | DNAUC oral h*uM | %F | Ue% po | LCMS |
|---|---|---|---|---|---|---|
| 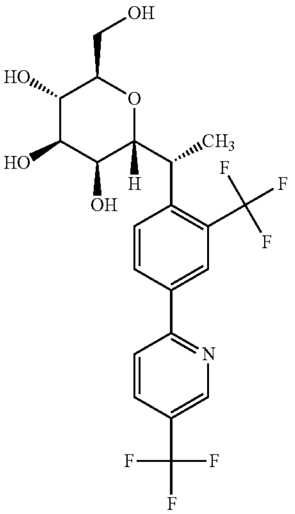 [SMILES: C[C@H](c1ccc(-c2ccc(C(F)(F)F)cn2)cc1C(F)(F)F)[C@H]1O[C@H](CO)[C@@H](O)[C@H](O)[C@@H]1O] | 33 | "+++" | | | | ESI-MS $[M + H]^+$ Calc'd for ($C_{21}H_{21}F_6NO_5H^+$), 482.14, found, 482.14 |
| 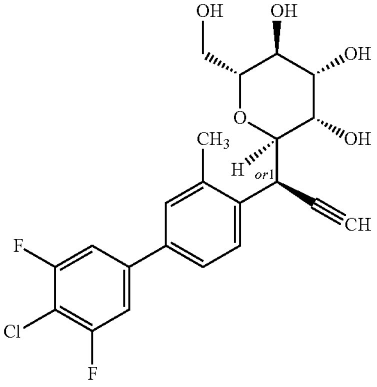 ISOMER 1 | 34 | "+++" | | | | ESI-MS [M + H]+ Calc'd for (C22H21ClF2O5H+), 439.11, found, 439.105 |

| Legend for Table 1 | | | |
|---|---|---|---|
| | DNAUC oral h*uM n = 3 (DN = dose normalized) | % F | Ue % po |
| "+" | <0.5 h · μM | <10% | <0.5% |
| "++" | 0.5 ≤ x ≤ h · μM | 10 ≤ x ≤ 30% | 0.5 ≤ x ≤ 5% |
| "+++" | >1 h · μM | >30% | >5% |
| | HAI nM | | |
| | <50 | "++++" | |
| | 50-200 | "+++" | |
| | 201-1000 | "++" | |
| | >1000 | "+" | |

Protocols Used to Evaluate the Compounds of Invention

The activities of the Examples 1-34 compounds above as FimH antagonists/inhibitors were obtained by the following assay(s), and results are provided in Table 1. Results not provided mean that the activities have not yet been tested.

Hemagglutination Inhibition Assay (HAI)

The hemagglutination inhibition (HAI) assay was performed with UTI89 bacteria and guinea pig red blood cells, as previously described (S. J. Hultgren, W. R. Schwan, A. J. Schaeffer, J. L. Duncan Infect. Immun. 1986, 54, 613-620 and Jarvis, C.; Han, Z.; Kalas, V.; Klein, R.; Pinkner, J. S.; Ford, B.; Binkley, J.; Cusumano, C. K.; Cusumano, Z.; Mydock-McGrane, L.; Hultgren, S. J.; Janetka, J. W., Chem Med Chem 2016, 11, 367-373). Results are listed in Table 1. Values not listed were not tested.

General Assays for Obtaining AUC Oral h*μm, % F, and Ue % PO Values 1.1. Animals Male Wistar Han rats were purchased from Vital River Laboratory Animal Technology Co. Ltd (Beijing, China). The animals were approx. 6-8 weeks old with body weights of 200-300 g on the dosing date. The animals were housed in a 12-hour light/12-hour dark cycle environment and had free access to food and water. All animals were fed prior to dosing. Studies were approved by the Pharmaron Institutional Animal Care and Use Committee (IACUC).

1.2. Study Design

Male Wistar Han rats (n=3 per dose group) were assigned to 1 group as shown in the table below. Test article was administered as an intravenous infusion for 1 hour (1 mg/kg) at 5 mL/kg/h. After 48 h, animals received a single oral dose (5 mg/kg, free form) at a dose volume of 10 mL/kg, respectively. Blood samples were collected at various time points after IV infusion and PO administrations. Urine samples were collected at various time points after IV infusion and PO administrations (for some compounds).

| Group | Dose Level (mg/kg) | Infusion Rate (mL/kg/h) | Dose Volume (mL/kg) | Conc. (mg/mL) | Administration Route | No. of Animals |
|---|---|---|---|---|---|---|
| 1 | 1 | 5 | — | 0.2 | IV infusion | 3/Group |
| 2 | 5 | — | 10 | 0.5 | PO | 3/Group |

1.3. Formulation Preparation

Preparation of dosing for IV infusion administration (1 mg/kg):

Test article was dissolved in DMSO with vortexing and sonification to obtain a stock solution. An aliquot of the stock solution was mixed with 10% HP-β-CD in saline with vortexing to obtain a solution with concentration at 0.2 mg/mL of test article.

Preparation of dosing for PO administration (5 mg/kg):

Test article was added into 1% Methyl Cellulose with vortexing and sonication to obtain a homogeneous suspension with concentration at 0.5 mg/mL of test article.

1.4. Sample Collection

Blood Samples:

For IV infusion (1 mg/kg) administration, blood samples were collected from each animal at 0, 0.25, 0.5, 0.75, 1, 1.08, 1.25, 1.5, 1.75, 2, 3, 5, 8, 12, 24 hour post-dose.

For PO (5 mg/kg) administration, blood samples were collected from each animal at 0, 0.25, 0.5, 1, 1.5, 2, 3, 4, 6, 8, 12, 24 hour post-dose.

Blood samples (50 μL) were collected from each animal via jugular vein. These blood samples were placed into tubes containing $K_2EDTA$. Whole blood was mixed with same volume of water and inverted several times. The blood samples were stored at −75±15° C. until analysis.

Urine Samples:

For IV infusion (1 mg/kg) administration, urine samples were collected from each animal at 0-4, 4-8, 8-12, 12-24 hour post-dose.

For PO (5 mg/kg) administration, urine samples were collected (for some compounds) from each animal at 0-4, 4-8, 8-12, 12-24 hour post-dose.

Urine samples were collected continuously into containers maintained over dry ice at the intervals outlined below and stored at −80° C. prior to analysis.

1.5. Preparation of Standard Solutions for LC-MS/MS Analysis 10 mg/mL of test article stock solution was diluted with DMSO to obtain a 1 mg/mL standard stock solution (free form).

Calibration standard working solutions were prepared at concentrations of 5, 10, 20, 50, 100, 500, 1000, 5000 and 10000 ng/mL by serial dilution of the standard stock solution in 50% acetonitrile in water. Quality control working solutions at concentrations of 10, 500 and 8000 ng/mL were prepared by serial dilution of the standard stock solution in 50% acetonitrile in water. These QC samples were prepared on the day of analysis in the same way as calibration standards.

1.6. Sample Treatment

5 μL of each calibration standard working solution (5, 10, 20, 50, 100, 500, 1000, 5000 and 10000 ng/mL) was added to 50 μL of blank Wistar Han rat blood (Blank blood: water=1:1) or urine to achieve calibration standards of 0.5-1000 ng/mL (0.5, 1, 2, 5, 10, 50, 100, 500, 1000 ng/mL) in a total volume of 55 μL. Quality Control (QC) samples at 1 ng/mL (low), 50 ng/mL (mid), 800 ng/mL (high) for blood or urine were prepared independently for those used for the calibration curves. These QC samples were prepared on the day of analysis in the same way as calibration standards.

55 μL of standards, 55 μL of QC samples or 55 μL of unknown samples (50 μL of blood or urine with 5 μL 50% acetonitrile) were mixed to 200 μL of acetonitrile containing IS (dexamethasone) to precipitate proteins. Then the samples were vortexed for 30 sec. After centrifugation at 4° C., 4700 rpm for 30 min, and 5 μL of the supernatant was injected into the LC-MS/MS system for quantitative analysis.

1.7. Pharmacokinetic Analysis

Test article blood and urine concentrations for each animal following IV infusion at 1 mg/kg and PO at 5 mg/kg were used to calculate pharmacokinetic parameters by employing a non-compartmental analysis (Phoenix™ WinNonlin® 7.0). The linear trapezoidal algorithm was used for AUC calculation.

AUC oral h*μM: Area under the curve (AUC) of drug concentration in blood vs. time (units: h*μM) following oral administration % F: Oral bioavailability (%) derived from the ratio of dose-normalized AUC following PO and IV administration Ue % PO: Percentage of oral dose eliminated unchanged in urine or an estimater of that parameter generated from using the percentage of the iv dose eliminated in the urine times the oral bioavailability From the foregoing description, one skilled in the art can easily ascertain the essential characteristics of this invention, and without departing from the spirit and scope thereof, can make various changes and modifications of the invention to adapt it to various usages and conditions.

We claim:

1. A compound of Formula I, or a pharmaceutical salt thereof,

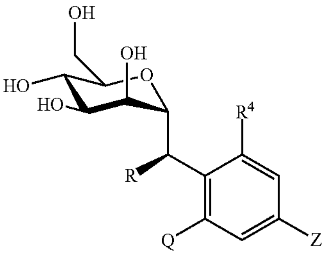

I in which

Z is

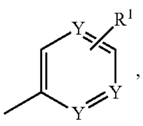 , 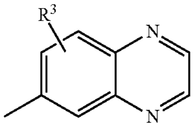 , 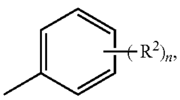 or

-continued

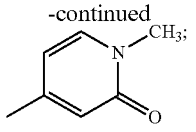

n=1 to 3;

Q is $CF_3$, $CH_3$ or Cl;

R is $C_{1-3}$alkyl (optionally substituted with up to 7 fluorine atoms), $C_{2-6}$alkynyl, phenyl, —$(CH_2)_m$—OH, optionally substituted cyclopropyl, or optionally substituted vinyl;

$R^1$, $R^2$, and $R^3$ are independently H, F, Cl, Br, $C_{3-6}$cycloalkyl, OR',—N($C_{1-6}$alkyl)$_2$, $C_{2-6}$alkenyl, $C_{2-6}$alkynyl, $C_{1-6}$alkyl (optionally substituted with up to 7 fluorine atoms, up to one hydroxy, up to one —N($C_{1-6}$ alkyl)$_2$, and up to one-O$C_{1-6}$alkyl), up to one-(CO)—NH—$CH_3$, or up to one cyano; provided $R^2$ cannot be all H at the same time;

$R^4$ is H or F;

R' is independently H or $C_{1-6}$ alkyl (optionally substituted with up to 7 fluorine atoms);

Y is independently CH, N or, where permitted by the structure of Z, $CR_1$, provided all Y's cannot be CH at the same time; and m=1 to 3.

2. A compound or pharmaceutically acceptable salt thereof according to claim 1, wherein Z is:

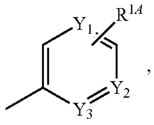

,

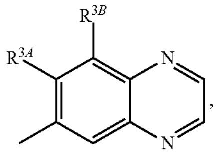

,

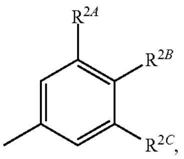

or

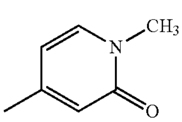

;

wherein $Y_1$ is N or $CR^{1B}$ and $Y_2$ and $Y_3$ are selected from the group consisting of N or CH, with the proviso that at least one of Y, $Y_2$ and $Y_3$ is N; and $R^{1A}$, $R^{1B}$, $R^{2A}$, $R^{2B}$, $R^{2C}$, $R^{3A}$ and $R^{3B}$ are independently selected from the group consisting of H, F, Cl, $CF_3$, cyclopropyl, —(CO)—NH—$CH_3$ and cyano, with the provisos that:

where $Y_1$ is $CR^{1B}$, one of $R^{1A}$ and $R^{1B}$ is H;

one of $R^{3A}$ and $R^{3B}$ is H;

at least one of $R^{2A}$, $R^{2B}$ and $R^{2C}$ is not H; and only one of $R^{2A}$, $R^{2B}$ and $R^{2C}$ may be —(CO)—NH—$CH_3$ or cyano.

3. A compound or pharmaceutically acceptable salt thereof according to claim 2, wherein Z is:

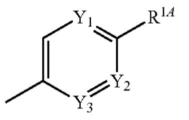

or

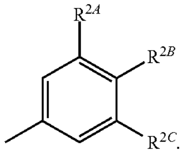

4. A compound or pharmaceutically acceptable salt thereof according to claim 3, wherein Z is:

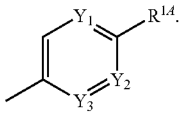

5. A compound or pharmaceutically acceptable salt thereof according to claim 4, wherein:

$Y_1$ and $Y_3$ are N and $Y_2$ is CH; and $R^{1A}$ is cyclopropyl or —$CF_3$.

6. A compound or pharmaceutically acceptable salt thereof according to claim 4, wherein:

$Y_3$ is N, $Y_2$ is CH and $Y_1$ is $CR^{1B}$; and one of $R^{1A}$ and $R^{1B}$ is H and the other is selected from the group consisting of —$CF_3$ or cyano.

7. A compound or pharmaceutically acceptable salt thereof according to claim 3, wherein Z is:

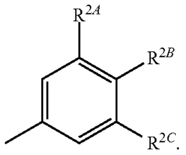

8. A compound or pharmaceutically acceptable salt thereof according to claim 7, wherein $R^{2A}$ is selected from the group consisting of H, F, CN and —(CO)—NH—$CH_3$; $R^{2B}$ is selected from the group consisting of H, CN and Cl; and $R^{2C}$ is selected from the group consisting of F and H; with the proviso that at least one of $R^{2A}$, $R^{2B}$ and $R^{2C}$ is not H, and with the proviso that only one of $R^{2A}$, $R^{2B}$ and $R^{2C}$ may be cyano.

9. A compound or pharmaceutically acceptable salt thereof according to claim 8, wherein $R^{2A}$ is F, $R^{2B}$ is selected from the group consisting of H and Cl; and $R^{2C}$ is F.

10. A compound or pharmaceutically acceptable salt thereof according to claim 1, wherein either Q is $CH_3$ and $R^4$ is H, or Q is $CF_3$ and $R^4$ is H.

11. A compound or pharmaceutically acceptable salt thereof according to claim 10, wherein Q is $CH_3$ and $R^4$ is H.

12. A compound or pharmaceutically acceptable salt thereof according to claim 1, wherein R is methyl or vinyl.

13. A compound or pharmaceutically acceptable salt thereof according to claim 1, wherein R is methyl.

14. A compound according to claim 1, that is selected from the group consisting of:

(2R,3S,4R,5S,6R)-2-(Hydroxymethyl)-6-((R)-1-(2-methyl-4-(5-(trifluoromethyl)pyrazin-2-yl)phenyl)ethyl)tetrahydro-2H-pyran-3,4,5-triol;

(2R,3S,4R,5S,6R)-2-(Hydroxymethyl)-6-((R)-1-(2-methyl-4-(4-(trifluoromethyl)pyridin-2-yl)phenyl)ethyl)tetrahydro-2H-pyran-3,4,5-triol;

(2R,3S,4R,5S,6R)-2-(hydroxymethyl)-6-((R)-1-(2-(trifluoromethyl)-4-(5-(trifluoromethyl)pyrazin-2-yl)phenyl)ethyl)tetrahydro-2H-pyran-3,4,5-triol;

(2R,3S,4R,5S,6R)-2-(Hydroxymethyl)-6-((R)-1-(2-methyl-4-(5-(trifluoromethyl)pyridin-3-yl)phenyl)ethyl)tetrahydro-2H-pyran-3,4,5-triol;

(2R,3S,4R,5S,6R)-2-(Hydroxymethyl)-6-((R)-1-(2-methyl-4-(5-(trifluoromethyl)pyrazin-2-yl)phenyl)propyl)tetrahydro-2H-pyran-3,4,5-triol;

(2R,3S,4R,5S,6R)-2-(Hydroxymethyl)-6-((R)-1-(2-methyl-4-(5-(trifluoromethyl)pyrazin-2-yl)phenyl)allyl)tetrahydro-2H-pyran-3,4,5-triol; and (2R,3S,4R,5S,6R)-2-((S)-1-(4'-chloro-3',5'-difluoro-3-methyl-[1,1'-biphenyl]-4-yl)-2-hydroxyethyl)-6-(hydroxymethyl)tetrahydro-2H-pyran-3,4,5-triol; or a pharmaceutically acceptable salt thereof.

15. A method for the treatment of a bacterial infection, Crohn's disease (CD), or Inflammatory Bowel Disease (IBD) comprising the administration of a therapeutically effective amount of a compound or a pharmaceutically acceptable salt thereof as defined in claim 1 to a human patient in need thereof.

16. A pharmaceutical composition comprising a compound or a pharmaceutically acceptable salt thereof as defined in claim 1 together with a pharmaceutically acceptable carrier.

17. The method according to claim 15, wherein the bacterial infection is an antibiotic-resistant bacterial infection.

18. The method according to claim 15, wherein the bacterial infection is a urinary tract infection (UTI).

19. The method according to claim 18, wherein the urinary tract infection is recurrent.

20. The method according to claim 18, wherein the urinary tract infection is chronic.

* * * * *